US006479653B1

(12) United States Patent
Natesan et al.

(10) Patent No.: US 6,479,653 B1
(45) Date of Patent: Nov. 12, 2002

(54) COMPOSITIONS AND METHOD FOR REGULATION OF TRANSCRIPTION

(75) Inventors: Sridaran Natesan, Chestnut Hill, MA (US); Michael Z. Gilman, Newton, MA (US)

(73) Assignee: ARIAD Gene Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/615,917

(22) Filed: Jul. 13, 2000

Related U.S. Application Data

(63) Continuation of application No. 09/140,149, filed on Aug. 26, 1998, now Pat. No. 6,117,680, which is a continuation-in-part of application No. 09/126,009, filed on Jul. 29, 1998, now abandoned, which is a continuation-in-part of application No. 08/920,610, filed on Aug. 27, 1997, now Pat. No. 6,015,709, which is a continuation-in-part of application No. 08/918,401, filed on Aug. 26, 1997, now abandoned.

(51) Int. Cl.[7] .............................................. C07H 21/04
(52) U.S. Cl. ..................... 536/23.4; 435/320.1; 435/325
(58) Field of Search .............................. 435/320.1, 325; 536/23.4

(56) References Cited

U.S. PATENT DOCUMENTS

| | | | |
|---|---|---|---|
| 5,215,909 A | 6/1993 | Soreq ........................ 435/325 |
| 5,573,925 A | 11/1996 | Halazonetis ............... 435/69.7 |
| 5,597,693 A | * 1/1997 | Evans et al. ................... 435/6 |
| 5,674,730 A | * 10/1997 | Baim et al. | |
| 5,723,329 A | 3/1998 | Mangelsdorf et al. ....... 435/348 |
| 5,830,462 A | 11/1998 | Crabtree et al. .......... 424/93.21 |
| 5,925,523 A | 7/1999 | Dove et al. .................... 435/6 |
| 5,961,974 A | * 10/1999 | Armitage et al. | |
| 5,989,808 A | 11/1999 | Young et al. ................... 435/6 |
| 6,133,027 A | 10/2000 | Yee et al. .................... 435/325 |

FOREIGN PATENT DOCUMENTS

| | | | |
|---|---|---|---|
| WO | WO 94/10308 | 5/1994 | |
| WO | WO-96/30512 A1 | * 10/1996 | |
| WO | WO 96/20951 A1 | * 11/1996 | |
| WO | WO 97/12040 | 4/1997 | |

OTHER PUBLICATIONS

Creighton (1984) Proteins, Structures and Molecular Principles, W. H. Freeman and Company, New York, p. 335.*
Knight et al (1989) Proc. Natl. Acad. Sci. USA 86: 797–801.*
Knight et al (1988) Biochemistry 27: 2088–2094, Abstract.*
Shi et al (1995) Mol. Cell. Biol. 15: 4309–4318.*
Horikoshi et al (995) Mol. Cell. Biol. 15: 227–234.*
Bonner et al (1992) Mol. Cell. Biol. 12: 1021–1030.*
Licht et al (1990) Nature 346: 76–79.*
Yang et al (1995) J. Biol. Chem. 270:15187–15193.
Becker et al (1989) Mol. Cell. Biol. 9:3878–3887.
Hollenberg et al (1988) Cell 55:899–906.
Qi et al (1995) Mol. Cell. Biol. 15:1817–1825.
Pomerantz et al (1995) Science 267:93–96.
Seipel et al (1992) EMBO Journal 11:4961–4968.
Zeng et al., (1997), Gene 185: 245–249.
Dang et al., (1991), Mol Cell Biol 11:954–962.
Hunger et al., (1996), Blood, 87:4607–4617.
Qian et al., (1995), J. Virology 69:4037–4044.
Sollerbrant et al., (1995) Nucleic Acids Research 23:588–594.
Mohamed et al., (1994) J. Steroid Biochem. Mol. Biol. 51:241–250.
Bustos et al., (1993) Proc Natl Acad Sci USA 90:5638–5642.
Chevray et al., (1992) Proc Natl Acad Sci USA 89:5789–5793.
Baim et al., (1991) Proc Natl Acad Sci USA 88:5072–5076.
Marchetti et al., (1995) J. Mol. Biol. 248:541–550.
Liu et al., (1997) European Biophysics Journal 25:399–403.
Hunger et al., (1994) Mol Cell Biol 14:5986–5996.
Simon et al., (1998) EMBO J. 17:6178–6187.
Kreusch et al., (1998) Nature 392:945–948.
Casasnovas et al., (1998) Proc Natl Acad Sci USA 95:4134–4139.
Poirier et al., (1998) Nature Structural Biology 5:765–769.
Blong et al., (1997) Biochem J. 327:747–757.
Kersten et al., (1997) J Biol Chem 272:29759–29768.
Kodadek and Johnston (1995) Chemistry and Biology 2:187–194.
Emami and Carey, (1992) EMBO J. 11:5005–5012.
Le Douarin et al., (1995) Nucleic Acids Research 23:876–878.
Granger–Schnarr et al., (1992) Proc Natl Acad Sci USA 89:4236–4239.
Suzuki–Yagawa et al., (1997) Mol Cell Biol 17:3284–3294.
Li and Brasler (1996) Molecular Endocrinology 10:252–264.
Morin et al., (1995) Cell Growth and Differentiation 6:789–798.
Blair et al., (1994) Mol Cell Biol 14:7226–7234.
Lin et al., (1994) J Biol Chem 269:17542–17549.
Ruben et al., (1992) Mol Cell Biol 12:444–454.
Morin et al., (1993) Nucleic Acids Research 21:2157–2163.
Guermah et al., (1998) Mol Cell Biol 18:3234–3244.
Schmitz and Baeuerle, (1991) EMBO J. 3805–3817.
Alberti et al., (1993) EMBO J. 12:3227–3236.
Zuo et al., (1994) Mol Cell Biol 14:7557–7568.

* cited by examiner

*Primary Examiner*—Remy Yucel
*Assistant Examiner*—Bronwer M. Loeb
(74) *Attorney, Agent, or Firm*—David L. Berstein

(57) ABSTRACT

The present invention relates to novel fusion proteins which activate transcription, to nucleic acid constructs encoding the proteins and their use in the genetic engineering of cells.

45 Claims, 10 Drawing Sheets

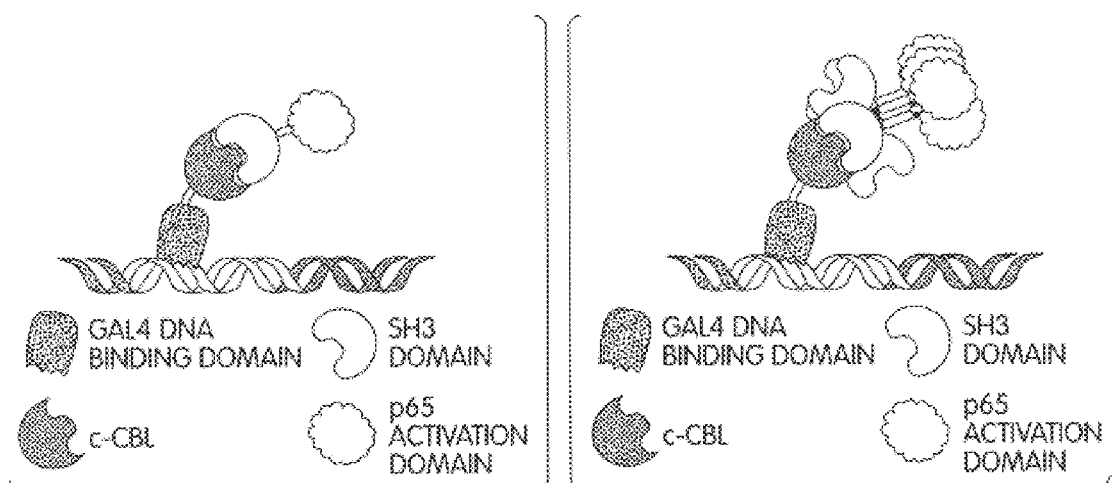
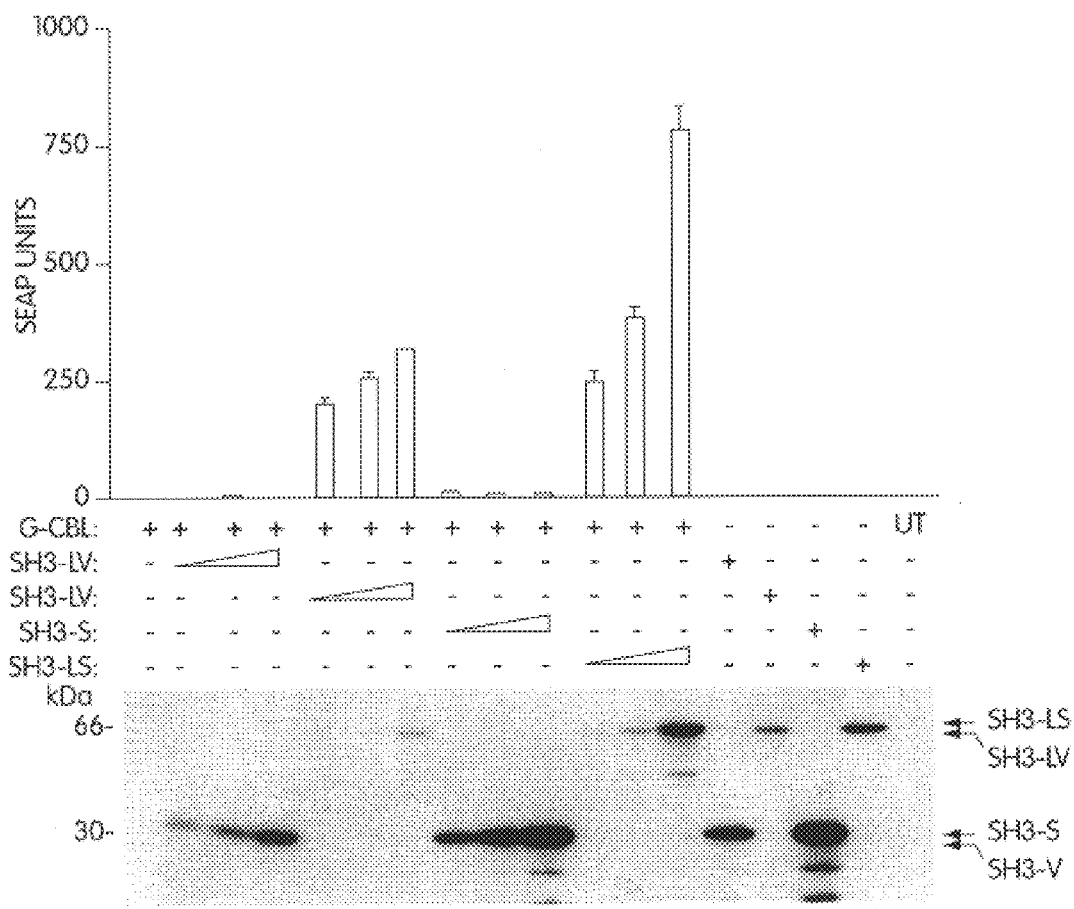
Fig. 6A  Fig. 6B
Fig. 6C

WT: 532-DFSSIADMDFSALLSQIS
M1: 532-DFSDFADMDFDADLSQIS
WT: 439-ALLQLQFDDED
M2: 439-ALLDLDFDDED
WT: 529-GDEDFSSIADMDFSALLSQI
M3: 529-GDEDASSIADMDASALLSQI
WT: 377-SALALPAPPQVL
M4: 377-GALALGAGGQVL
WT: 401-SALAQAPAPVP
M5: 401-GALAQAGAGVG
WT: 434-GTLSEALLQLQFD
M6: 434-GDFS-ALLQLQFD
WT: 472-SEFQQLLNQ
M7: 472-SEFSALLNQ
WT: 472-SEFQQLLNQ
M8: 472-SDFQQLLNQ
WT: 530-DEDFSSIADMDFS
M9: 530-DEDFSSLLDMDFS

Fig. 7

COMPOSITIONS AND METHOD FOR REGULATION OF TRANSCRIPTION

This application is a continuation of U.S. Ser. No. 09/140,149, filed Aug. 26, 1998, now U.S. Pat. No. 6,117,680, which is a continuation-part of U.S. Ser. No. 09/126,009, filed Jul. 29, 1998, now abandoned, which is a continuation-in-part of Ser. No. 08/920,610, filed Aug. 27, 1998, now U.S. Pat. No. 6,015,709, which is a continuation-in-part of Ser. No. 08/918,401, filed Aug. 26, 1997, now abandoned.

BACKGROUND OF THE INVENTION

Activation of transcription of a eukaryotic gene involves the interaction of a variety of proteins to form a complex that is recruited to the gene through protein:DNA interactions. Key protein domains on one or more of the components include transcription activation domains and DNA binding domains. Elucidating the mechanism of transcription, identifying and characterizing components of the transcriptional machinery and in some cases harnessing some of those components have been the subject of extensive research. (See, e.g., Brent and Ptashne, 1985; Hope and Struhl, 1986; Keegan et al. 1986., Fields and Song, 1989; Spencer et al, 1993, Belshaw et al, 1996 and Rivera et al, 1996)(A Bibliography is provided just prior to the Examples, below.)

Transcription activation domains are thought to function by recruiting a number of proteins with specific functions to the promoter (Lin and Green, 1991; Goodrich et al, 1993; Orphanides et al. 1996 and references cited therein; Ptashne and Gann, 1997 and references cited therein). Among the large number of activation domains that have been characterized to date, the acidic-activation domain of the Herpes Simplex virus encoded protein, VP16, is considered to be a very strong inducer of transcription and is widely used in biological research (Sadowski et al, 1988, Ptashne and Gann, 1997). The transcription activation domain of the p65 subunit of the human transcription factor NF-kB is also a very potent stimulator of gene expression, and in certain contexts can induce transcription more strongly than VP16 (Schmitz and Baeuete, 1991; Ballard et al, 1992; Moore at al, 1993, Blair et al, 1994; Natesan et al, 1997). Both the VP16 and p65 activation domains are thought to function by interacting with and recruiting a number of proteins to the promoter (Cress and Triezenberg, 1990; Scmitz at al, 1994; Uesugi et at, 1997).

One of the remarkable features of such activation domains is that "fusing" them to heterologous protein domains seldom affects their ability to activate transcription when recruited to a wide variety of promoters. The high degree of functional independence exhibited by these activation domains makes them valuable tools in various biological assays for analyzing gene expression and protein-protein or protein-RNA or protein-small molecule drug interactions (Fields and Song, 1989; Sengupta et al, 1996; Rivera et al, 1996; Triezenberg, 1995 and references cited therein). The ability to activate gene expression strongly and when recruited to a wide range of promoters makes both p65 and VP16 attractive candidates for activation of gene transcription in gene therapy and other applications. However, even more potent activation domains, if available, would be useful for achieving higher levels of transcription on a per cell basis, and for improving the efficiency of the many biological assays that rely upon activation of transcription of a reporter gene.

Several strategies to improve the potency of activation domains and thereby the expression of genes under their control have been reported (Emami and Carey, 1992; Gerber at al, 1994; Ohashi et al, 1994; Blair at al, 1996; Tanaka et al, 1996). These approaches generally involve increasing the number of copies of activation domains fused to the DNA binding domain or generating activators containing synergizing combinations of activation domains. Although some activators generated by these methods have been shown to be more potent, a number of limitations preclude their widespread application. First, potent activators comprising reiterated activation domains do not increase the absolute levels of reporter gene expression when tested on promoters with multiple binding sites for the activator (Emami and Carey, 1992). Second, a number of synergistic combinations of activation domains reported in the literature involve weak activation domains and the absolute levels of gene expression induced by these synergizing activation domains are much lower compared to potent acidic activation domains from VP16 or p65 (Gerber at al, 1994; Tanaka et al, 1996). Third, it is not known whether any of these potent activation domains are capable of inducing gene transcription strongly when they are non-covalently linked to the DNA binding domain. Fourth, many potent activators containing multiple copies of VP16 or other acidic activators are highly toxic and/or accumulate to only low levels in the cell.

As mentioned at the outset, a variety of important applications involving gene transcription require or would benefit from higher levels of gene expression. As noted above, however, efforts to improve the potency of activation domains have been disappointing. Moreover, expression of various transcription activators revealed that observed levels of more potent activators, such as the p65 unit of NF-kB, are lower than expected. Without wishing to be bound by any one theory, we suggest that the more potent the activation domain, the more toxic it is to the cell, the more disfavored is its expression and/or the less of it is observed to accumulate in cells. How, then, is it possible to increase levels of heterologous gene expression? Remarkably, we have found that it is still possible to outmaneuver these facts of nature to improve heterologous gene expression and have in fact done so using the principles of "bundling", the engineering of the transcription activation domain, and combinations thereof, as described below.

SUMMARY OF THE INVENTION

This document discloses new improvements in the design and delivery of transcription activation domains and provides improved materials and methods for regulating the transcription of a target gene. Aspects of the invention are applicable to systems involving either covalent or non-covalent linking of the transcription activation domain to a DNA binding domain.

Key features of the invention include "bundling" domains, fusion proteins containing them, recombinant nucleic acids encoding such fusion proteins, systems involving bundles of such fusion proteins, and other materials and methods involving such bundling domains. Key fusion proteins of the invention contain at least two mutually heterologous domains, one of which being a bundling domain. An important design concept is that the fusion proteins do not need to act alone. Instead, they find and bind to each other (or with other proteins containing the bundling domain) to form a posse to accomplish their mission. In practice, cells are engineered by the introduction of recombinant nucleic acids encoding the fusion proteins, and in some cases with additional nucleic acid constructs, to render them capable of ligand-dependent regulation of transcription of a target gene. Administration of the ligand to the cells then regulates (positively, or in some cases, negatively) target gene transcription.

Detailed information concerning bundling domains, guidance on their use and illustrative examples are provided below. Generally speaking, bundling domains include any domain that induces proteins that contain it to form multimers ("bundles") through protein-protein interactions with each other or with other proteins containing the bundling domain. Examples of bundling domains that can be used in the practice of this invention include domains such as the lac repressor tetramerization domain, the p53 tetramerization domain, a leucine zipper domain, and domains derived therefrom which retain observable bundling activity. Proteins containing a bundling domain are capable of complexing with one another to form a bundle of the individual protein molecules. Such bundling is "constitutive" in the sense that it does not require the presence of a cross-linking agent (i.e., a cross-linking agent which doesn't itself contain a proteinaceous bundling domain) to link the protein molecules.

Illustrative (non-limiting) examples of heterologous domains which can be included along with a bundling domain in various fusion proteins of this invention include transcription regulatory domains (i.e., transcription activation domains such as a p65, VP16 or AP domain; transcription potentiating or synergizing domains; or transcription repression domains such as an ssn-6/TUP-1 domain or Krüppel family suppressor domain); a DNA binding domain such as a GAL4, lex A or a composite DNA binding domain such as a composite zinc finger domain or a ZFHD1 domain; or a ligand-binding domain comprising or derived from (a) an immunophilin, cyclophilin or FRB domain; (b) an antibiotic binding domain such as tetR: or (c) a hormone receptor such as a progesterone receptor or ecdysone receptor.

A wide variety of ligand binding domains may be used in this invention, although ligand binding domains which bind to a cell permeant ligand are preferred. It is also preferred that the ligand have a molecular weight under about 5 kD, more preferably below 2.5 kD and optimally below about 1500 D. Non-proteinaceous ligands are also preferred. Ligand binding domains include, for example, domains selected or derived from (a) an immunophilin (e.g. FKBP 12), cyclophilin or FRAP domain; (b) a hormone receptor such as a receptor for progesterone, ecdysone or another steroid; and (c) an antibiotic receptor such as a tetR domain for binding to tetracycline, doxycycline or other analogs or mimics thereof.

Examples of ligand binding domain/ligand pairs that may be used in the practice of this invention include, but are not limited to: FKBP:FK1012, FKBP:synthetic divalent FKBP ligands (see WO 96/0609 and WO 97/31898), FRB:rapamycin/FKBP (see e.g., WO 96/41865 and Rivera et al, "A humanized system for pharmacologic control of gene expression", Nature Medicine 2(9):1028–1032 (1997)), cyclophilin:cyclosporin (see e.g. WO 94/18317), DHFR:methotrexate (see e.g. Licitra et al, 1996, Proc. Natl. Acad. Sci. USA 93:12817–12821), TetR:tetracycline or doxycydine or other analogs or mimics thereof (Gossen and Bujard, 1992, Proc. Natl. Acad. Sci. U.S.A. 89:5547; Gossen et al, 1995, Science 268:1766–1769; Kistner et al, 1996, Proc. Natl. Acad. Sci. USA 93:10933–10938), a progesterone receptor:RU486 (Wang et al, 1994, Proc. Natl. Acad. Sci. USA 91:8180–8184), eodysone receptor ecdysone or muristerone A or other analogs or mimics thereof (No et al, 1996, Proc. Natl. Acad. Sci. USA 93:3346–3351) and DNA gyrase:coumermycin (see e.g. Farrar et al, 1996, Nature 383:178–181).

A wide variety of DNA binding domains may be used in the practice of this invention, including a domain selected or derived from a GAL4, lexA or composite (e.g. ZFHD1) DNA binding domain, or a DNA binding domain, e.g., in combination with ligand binding domains such as a wt or mutated progesterone receptor domain. TetR domains, which provide both DNA binding and ligand binding functions, are discussed in the context of ligand binding domains. In many applications it is preferable to use a DNA binding domain which is heterologous to the cells to be engineered. Heterologous DNA binding domains include those which occur naturally in cell types other than the cells to be engineered as well as composite DNA binding domains containing component portions which are not found in the same continuous polypeptide or gene in nature, at least not in the same order or orientation or with the same spacing present in the composite domain. In the case of composite DNA binding domains, component peptide portions which are endogenous to the cells or organism to be engineered are generally preferred.

In the case of the chimeric transcription factors containing a tetR domain, the DNA binding domain is provided by the tetR component, and is by its nature heterologous to eukaryotic cells. TetR domains are discussed in further detail in the context of ligand binding domains.

In embodiments in which an endogenous gene is to be regulatably expressed, a composite DNA binding domain which is selected for recognition of one or more sequences upstream of the target gene may be deployed.

Additional information concerning DNA binding domains is provided below.

In an important application of this invention, two or more of the fusion proteins in the bundle each comprise, in addition to the bundling domain, at least one transcription activation domain which is heterologous to the bundling domain. Bundling of proteins containing transcription activation domains can significantly increase their effective potency (relative to a single such fusion protein lacking a bundling domain) and consequently leads to strong induction of gene expression. Unlike their counterparts lacking a bundling domain, fusion proteins containing a bundling domain are designed to achieve effective local concentrations of transcription activation domains and to robustly induce gene expression when recruited en masse to an expression control sequence—even despite relatively low overall levels of expression or accumulation of the fusion proteins. Highly potent bundled activation domains can also be used in a wide variety of assays having transcriptional read outs. Such assays include assays for identifying protein-protein interactions (or inhibitors thereof) in a eukaryotic, preferably mammalian, two-hybrid assay or variant thereof, e.g., three-hybrid assay, reverse two-hybrid assay, etc.

Bundling domains may be introduced into the design of fusion proteins of a variety of regulated gene expression systems, including both allostery-based systems such as those regulated by tetracycline, RU486 or eodysone, or analogs or mimics thereof, and dimerizaion-based systems such as those regulated by divalent compounds like FK1012, FKCsA, rapamycin, AP1510 or coumermycin, or analogs or mimics thereof, all as described below (See also, Clackson, 1997, Controlling mammalian gene expression with small molecules, Current Opinion in Chem. Biol. 1:210–218). The fusion proteins may comprise any combination of relevant components, including bundling domains, DNA binding domains, transcription activation (or repression) domains and ligand binding domains. Other heterologous domains may also be included.

Various embodiments of this invention involve fusion proteins which contain at least one bundling domain, DNA binding domain and transcription activation domain; at least one bundling domain, ligand binding domain and transcription repression domain; at least one bundling domain, ligand binding domain and DNA binding domain; at least one bundling domain, ligand binding domain, DNA binding domain and transcription activation domain; and, preferably, at least one bundling domain, ligand binding domain and transcription activation domain. In currently preferred embodiments, these fusion proteins represent improvements on the type described in WO94/18317 and WO96/41865, wherein the ligand binding domain is or is derived from a cyclophilin, immunophilin (e.g. an FKBP domain) or FRB domain-although, any ligand binding domain may be used in the chimeric proteins, and the regulatory mechanism can be dimerization- or allostery-based.

A preferred fusion protein contains a lac repressor tetramerization domain, an FRB domain and a transcription activation domain derived from the activation domain of human p65. It should be appreciated that in any of the embodiments of this invention involving a fusion protein containing at least one transcription activation domain derived from p65, whether with or without a bundling domain, the p65 peptide sequence may be a naturally occurring p65 sequence or may be engineered as described below.

Another aspect of this invention involves improvements in the transcription activation domain itself. In this regard, recombinant nucleic acids are provided which encode fusion proteins containing a transcription activation domain and at least one additional domain that is heterologous thereto, where the peptide sequence of the activation domain is itself modified relative to the naturally occurring sequence from which it was derived to increase or decrease its potency as a transcriptional activator relative to the counterpart comprising the native peptide sequence. Certain embodiments of this invention involve fusion proteins containing a transcription activation domain derived from p65 and bearing one or more of the mutations shown in FIG. 7. Fusion proteins containing one or more modified activation domains can also contain a bundling domain to further increase their efficacy as transcriptional activators, and/or one or more additional domains such as a ligand binding domain, DNA binding domain or transcription activation synergizing domain, such as are noted above and as discussed below.

The invention thus provides recombinant nucleic acid constructs which encode the various proteins of this invention or are otherwise useful for practicing it, various DNA vectors containing those constructs for use in transducing prokaryotic and eukaryotic cells, cells transduced with the recombinant nucleic acids, fusion proteins encoded by the above recombinant nucleic acids, and target gene constructs.

Also provided are nucleic acid compositions comprising two or more recombinant nucleic acids which, when present within a cell, permit transcription of a target gene, preferably following exposure to a cell permeant ligand. These compositions are illustrated as follows:

Composition #1. A first such composition comprises a recombinant nucleic acid encoding a fusion protein comprising at least one ligand binding domain, bundling domain and transcription activation domain; a second recombinant nucleic acid encoding a fusion protein comprising a DNA binding domain and at least one ligand binding domain; and an optional third recombinant nucleic acid comprising a target gene (or cloning site) operatively linked to an expression control sequence including a DNA sequence recognized by the DNA binding domain mentioned above. Such compositions are illustrated by embodiments in which the ligand binding domains are or are derived from immunophilin, cyclophilin or FRB domains; the transcription activation domain is or is derived from an activation domain such as a VP16 or p65 domain; and the bundling domain is or is derived from a lac repressor tetramerization domain.

Composition #2. Another such composition is similar to Composition #1 except that the fusion protein encoded by the first recombinant nucleic acid comprises at least one ligand binding domain, bundling domain and DNA binding domain, and the fusion protein encoded by the second recombinant nucleic acid comprises a transcription activation domain and at least one ligand binding domain.

Composition #3. Another such composition comprises a recombinant nucleic acid encoding a fusion protein comprising at least one ligand binding domain, bundling domain and transcription activation domain; a second recombinant nucleic acid encoding a protein comprising a DNA binding domain; and an optional third recombinant nucleic add comprising a target gene (or cloning site) operatively linked to an expression control sequence including a DNA sequence recognized by the DNA binding domain mentioned above. Such compositions are illustrated by embodiments in which the ligand binding domains are or are derived from a receptor domain such as an ecdysone receptor; the DNA binding domain is or is derived from a DNA binding domain such as an RXR protein, chosen for its ability to bind to the receptor domain in the presence of a ligand for that receptor; the transcription activation domain is or is derived from an activation domain such as a VP16 or p65 domain; and the bundling domain is or is derived from a lac repressor tetramerization domain.

Composition #4. Another such composition comprises a recombinant nucleic acid encoding a fusion protein comprising at least one ligand binding domain, DNA binding domain, bundling domain and transcription activation domain (where the ligand binding domain and DNA binding domain may be part of or derived from the same domain); and an optional second recombinant nucleic acid comprising a target gene (or cloning site) operatively linked to an expression control sequence including a DNA sequence recognized by the DNA binding domain mentioned above. Such compositions are illustrated by embodiments in which the ligand binding and DNA binding domains are or are derived from a receptor domain such as a tetracycline receptor which is capable of binding to a characteristic DNA sequence in the presence of tetracycline or another ligand for the receptor; the transcription activation domain is or is derived from an activation domain such as a VP16 or p65 domain; and the bundling domain is or is derived from a lac repressor tetramerization domain. Such compositions are further illustrated by embodiments in which the ligand binding domain is or is derived from a receptor domain such as a progesterone receptor which is capable of binding to progesterone or analogs or mimics thereof, including RU486; the DNA binding domain is or is derived from a GAL4 or composite DNA binding domain; the transcription activation domain is or is derived from an activation domain such as a VP16 or p65 domain; and the bundling domain is or is derived from a lac repressor tetramerization domain.

Composition #5. Another such composition, which unlike Compositions 1–4 is designed for constitutive expression rather than for ligand-mediated regulation of transcription, comprises a recombinant nucleic acid encoding a fusion protein comprising at least one DNA binding domain, bundling domain and transcription activation domain; and a second recombinant nucleic acid comprising a target gene (or cloning site) operatively linked to an expression control sequence including a DNA sequence recognized by the DNA binding domain mentioned above. Such compositions are illustrated by embodiments in which the transcription activation domain is or is derived from an activation domain such as a VP16 or p65 domain; the DNA binding domain is or is derived from a GAL4 or composite DNA binding domain; and the bundling domain is or is derived from a lac repressor tetramerization domain.

Compositions 1, 3, 4 and 5 may further comprise an additional recombinant nucleic acid encoding a fusion protein comprising a bundling domain and at least one transcription activation domain or transcription synergizing domain, with or without one or more optional additional domains.

Each of the recombinant nucleic acids of this invention may further comprise an expression control sequence operably linked to the coding sequence and may be provided within a DNA vector, e.g., for use in transducing prokaryotic or eukaryotic cells. Some or all of the recombinant nucleic acids of a given composition as described above, including any optional recombinant nucleic acids, may be present within a single vector or may be apportioned between two or more vectors. In certain embodiments, the vector or vectors are viral vectors useful for producing recombinant viruses containing one or more of the recombinant nucleic acids. The recombinant nucleic acids may be provided as inserts within one or more recombinant viruses which may be used, for example, to transduce cells in vitro or cells present within an organism, including a human or non-human mammalian subject. For example, the recombinant nucleic acids of any of Compositions 1–5, including any optional recombinant nucleic acids, may be present within a single recombinant virus or within a set of recombinant viruses, each of which containing one or more of the set of recombinant nucleic acids. Viruses useful for such embodiments include any virus useful for gene transfer, including adenoviruses, adeno-associated viruses (AAV), retroviruses, hybrid adenovirus-AAV, herpes viruses, lenti viruses, etc. In specific embodiments, the recombinant nucleic acid comprising the target gene is present in a first virus and one or more or the recombinant nucleic acids encoding the transcription regulatory protein(s) are present in one or more additional viruses. In such multiviral embodiments, a recombinant nucleic add encoding a fusion protein comprising a bundling domain and a transcription activation domain, and optionally, a ligand binding domain, may be provided in the same recombinant virus as the target gene construct, or alternatively, on a third virus. It should be appreciated that non-viral approaches (naked DNA, liposomes or other lipid compositions, etc.) may be used to deliver recombinant nucleic acids of this invention to cells in a recipient organism.

The invention also provides methods for rendering a cell capable of regulated expression of a target gene which involves introducing into the cell one or more of the recombinant nucleic acids of this invention to yield engineered cells which can express the appropriate fusion protein(s) of this invention to regulate transcription of a target gene. The recombinant nucleic acid(s) may be introduced in viral or other form into cells maintained in vitro or into cells present within an organism. The resultant engineered cells and their progeny containing one or more of these recombinant nucleic acids or nucleic acid compositions of this invention may be used in: a variety of important applications discussed elsewhere, including human gene therapy, analogous veterinary applications, the creation of cellular or animal models (including transgenic applications) and assay applications. Such cells are useful, for example, in methods involving the addition of a ligand, preferably a cell permeant ligand, to the cells (or administration of the ligand to an organism containing the cells) to regulate expression of a target gene. Particularly important animal models include rodent (especially mouse and rat) and non-human primate models. In gene therapy applications, the cells will generally be human and the peptide sequence of each of the various domains present in the fusion proteins (with the possible exception of the bundling domain) will preferably be, or be derived from, a peptide sequence of human origin.

In certain assay applications, recombinant nucleic acids are designed as described for Composition #1, except that the ligand binding domains of the fusion proteins are replaced with protein domains that are known to bind to each other. Cells transduced with these recombinant nucleic acids and with a matched target gene construct express a target gene typically selected for convenience of measurement of expression level. These cells can be used to identify the presence of a substance which blocks the interaction of the two protein domains which are known to interact.

In other 2-hybrid-type applications aimed at the identification of genes encoding proteins which interact with a protein or protein domain of interest, cells are transduced with similar recombinant nucleic acids as described immediately above, except that a library of test nucleic acid sequences of potential interest is cloned into one of the recombinant nucleic acids encoding one of the fusion proteins. A 2-hybrid style assay is conducted in which transcription of the target gene indicates the presence of a test nucleic acid sequence which encodes a domain that interacts with the protein domain in the cognate fusion protein.

Reverse 2-hybrid-type assays may be conducted analogously using cells engineered to positively or negatively regulate expression of a reporter gene as a result of "2-hybrid" formation. The cells are exposed to one or more test substances, and inhibition of regulation of expression is taken as an indication of possible inhibition of the 2-hybrid formation.

BRIEF DESCRIPTION OF THE FIGURES

Abbreviations used in the Figures:

G=yeast GAL4 DNA binding domain, amino acids 1–94

F=human FKBP12, amino acids 1–107

R=FRB domain of human FRAP, amino acids 2025–2113

S=activation domain from the p65 subunit of human NF-kB, amino acids 361–550

V=activation domain from Herpesvirus VP16, amino acids 410–494

L=*E. coli* lactose repressor, amino acids 46–360

MT=Minimal Tetramerization ("bundling") domain of *E. coli* lactose repressor, amino acids 324–360

FIG. 1A–1H Diagram comparing various fusion proteins, with and without bundling domains, and their use in various strategies for delivery of activation domains to the promoter of a target gene. (A) two fusion proteins, one containing a DNA binding domain (e.g. a GAL4 or ZFHD1 DNA binding domain) fused to an FKBP12, and the other containing a p65 activation domain fused to an FRB, are expressed in cells. Addition of rapamycin leads to the recruitment of a singe activation domain to each DNA binding domain monomer. (B) Fusion of multiple FKBPs to the DNA binding domain allows rapamycin to recruit multiple activation domains to each DNA binding domain monomer. (C) Addition of the lactose repressor tetramerization domain to the FRB-activation domain fusion allows rapamycin to recruit four activation domains to each FKBP fused to the DNA binding domain (D) Rapamycin recruits bundled activation domain fusion protein to each of the FKBP-DNA binding domain fusion proteins. (E) and (F) illustrate a mutated tetR-based system, without and with bundling. (G) and (H) illustrate an engineered progesterone-R-based system, without and with bundling.

Figure 2A:
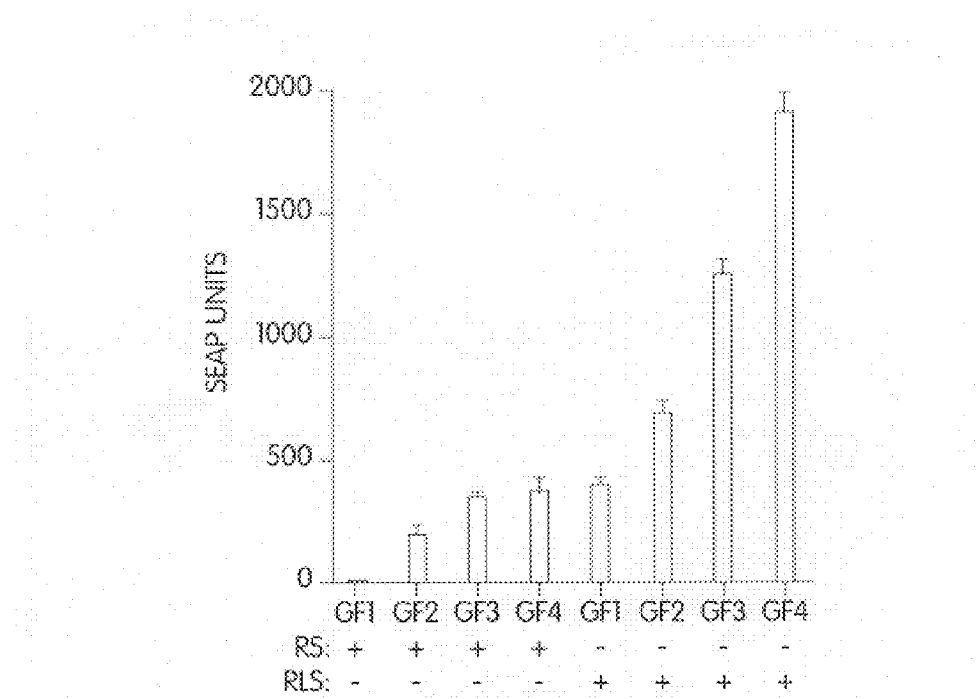

FIG. 2A Expression levels of the stably integrated reporter gene correlate with the number of activation domains recruited to the promoter. The indicated DNA binding domain and activation domain fusions were transfected into HT1080B cells containing a stably integrated SEAP reporter. Mean values of SEAP activity secreted into the medium following addition of 10 nM rapamycin are shown (+/−S.D.). In all cases, SEAP expression values are plotted for cultures receiving 100 ng of activation domain expression plasmid, which gives peak expression values in transiently transfected cells and slightly below peak levels in the stably transfected cell line.

Figure 2B:
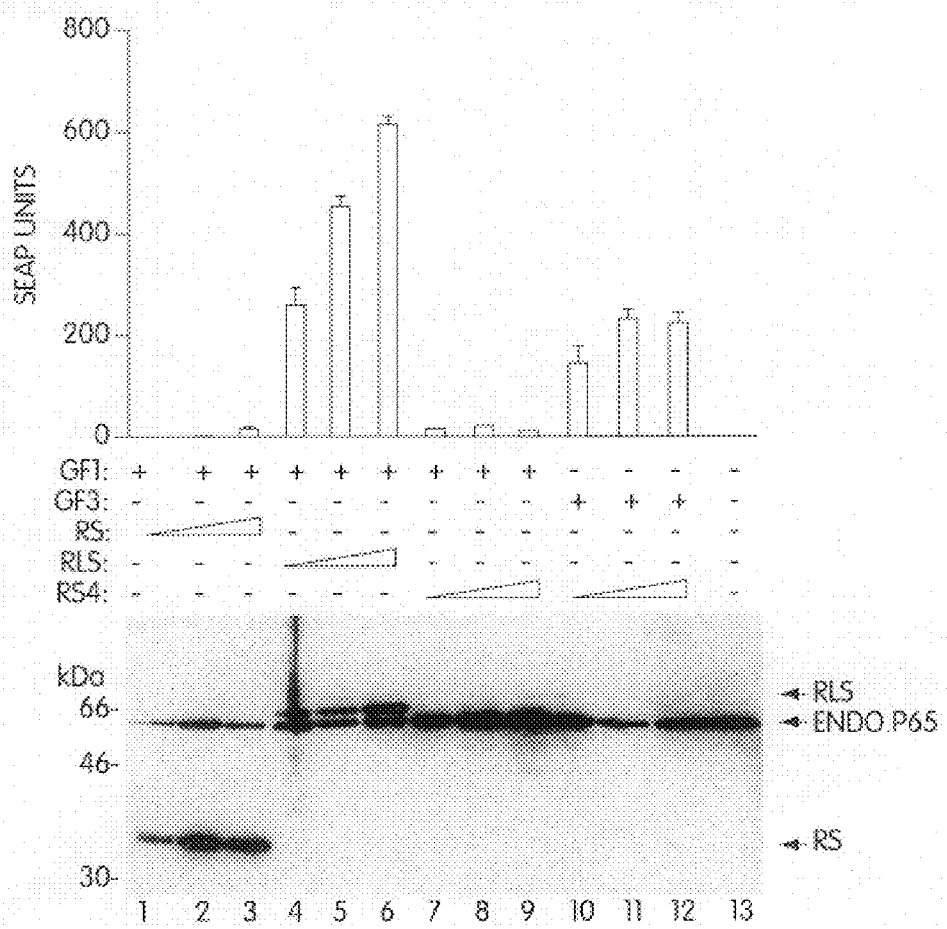

FIG. 2B Expression levels of the stably integrated reporter gene correlate with the number of activation domains recruited to the promoter. The indicated DNA binding domain and activation domain fusions were transfected into HT1080B cells containing a stably integrated SEAP reporter. Mean values of SEAP activity secreted into the medium following addition of 10 nM rapamycin are shown (+/−S.D.). A Western blot indicating expression levels of the various fusion proteins is also shown.

Figure 3A:
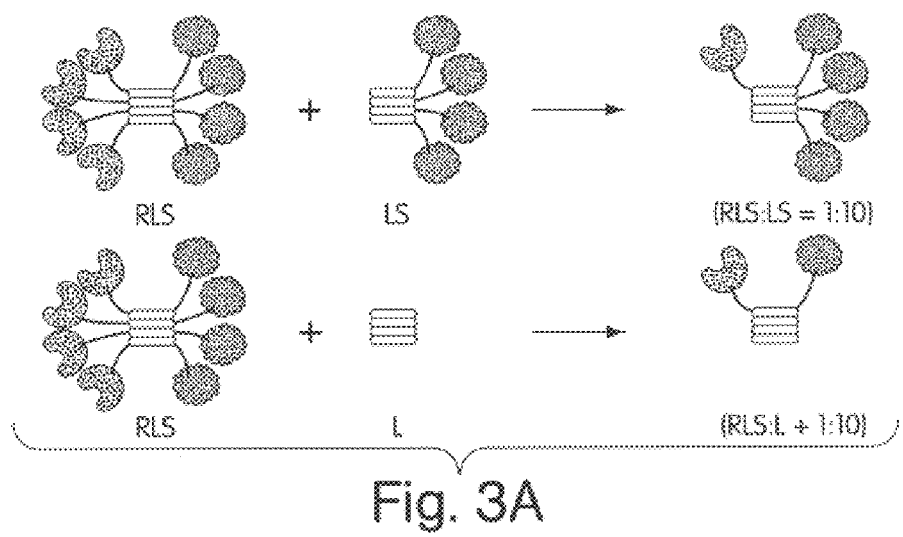

FIG. 3A Synergy between the activation domains in the RLS bundle is the primary cause for the super-activation of the reporter gene expression Schematic illustration of the composition of the protein bundles of RLS with increasing concentration of co-expressed LS or L in the cell.

Figure 3B:
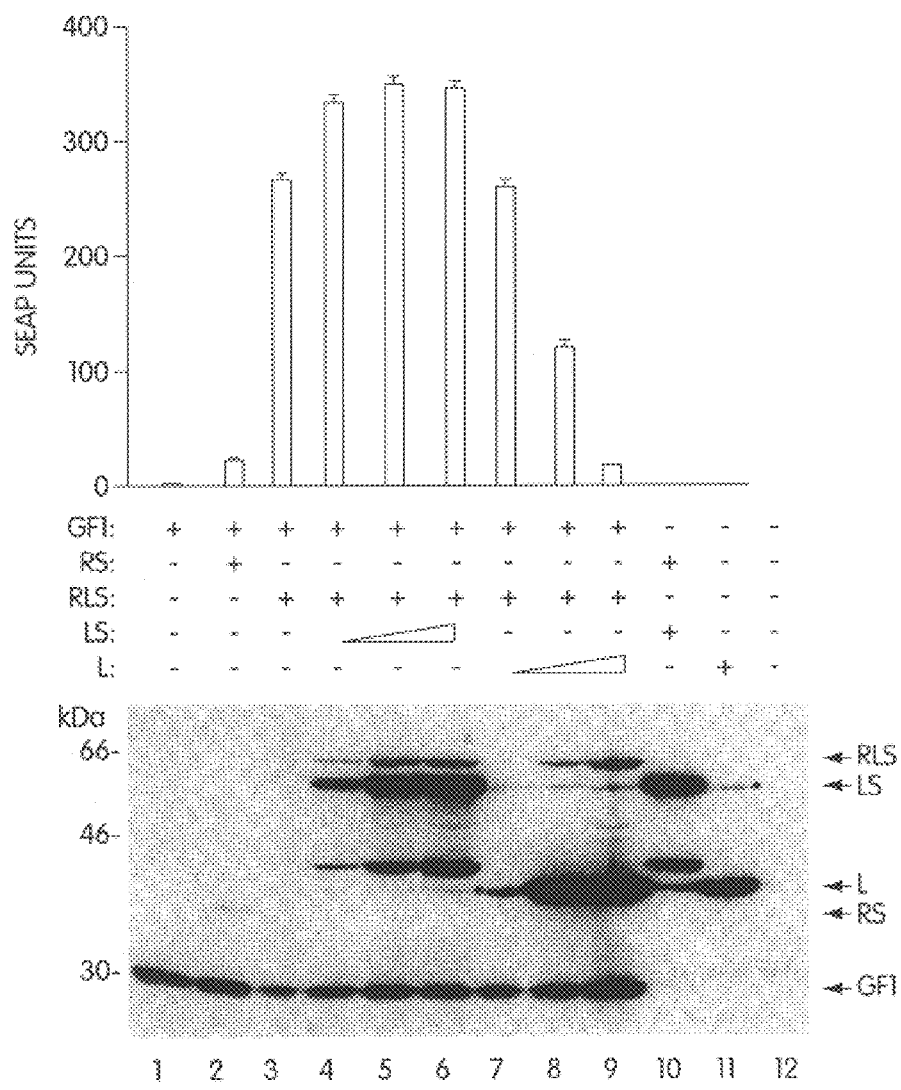

FIG. 3B Twenty nanograms of GF1 encoding plasmid was co-transfected with 100 ng of RLS alone or with indicated concentrations of LS or L regions. The cells were stimulated with 10 nM rapamycin and the SEAP activity in the medium was measured 18 hrs after transfection. Mean values of SEAP activity secreted into the medium following addition of rapamycin are shown (+/−S.D.).

FIG. 3C Western blot analyses using 12CA5 antibody against hemagglutinin epitope of various recombinant proteins expressed in the transfected cells is shown.

Figure 4:
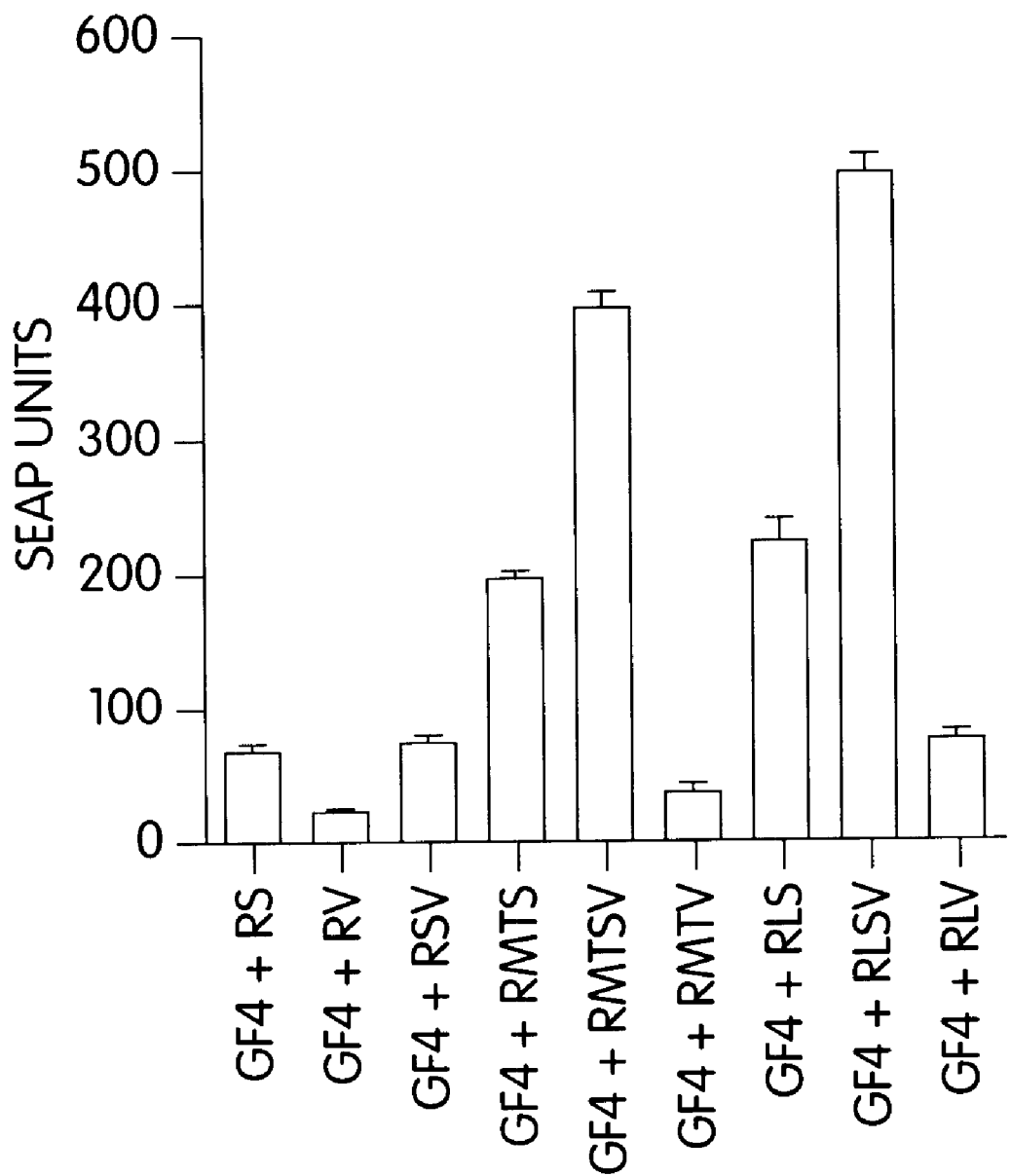

FIG. 4 A thirty-six amino acid region in the carboxy terminal of the lactose repressor protein is sufficient for generating highly potent and bundled activation domain fusion proteins. HT1080 B cells were co-transfected with 20 ng GF1 and 100 ng of indicated activation domain containing plasmid vectors. Transcription of the reporter gene was stimulated by the addition of 10 nM rapamycin in the medium. Mean values of SEAP activity secreted into the medium assayed 24 hrs after transfection are shown (+/−S.D.)

Figure 5A:
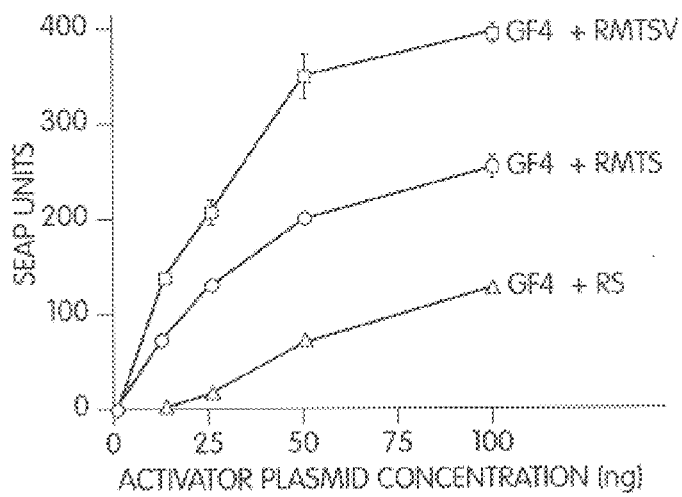

FIG. 5A Tethering bundled activation domain fusion proteins to DNA binding proteins significantly reduces the amount of reconstituted activators required to strongly stimulate the target gene expression. Twenty nanograms of GF4 and indicated concentrations of activation domain expressing plasmids were transfected into HT1080 B cells. Transcription of the stably integrated reporter gene was induced by the addition of 10 nM rapamycin in the medium.

Figure 5B:
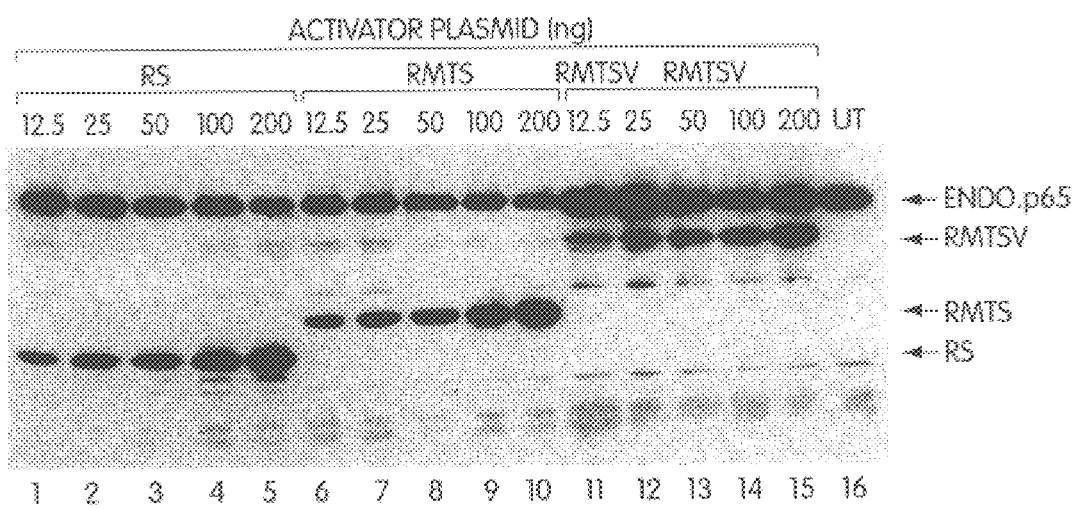

FIG. 5B Western blot analysis of the relative expression levels of the transfected transcription factors.

Figure 5C:
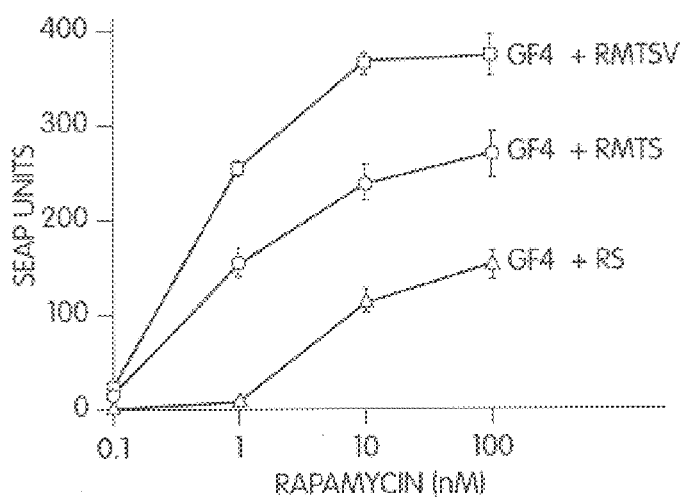

FIG. 5C Twenty nanograms of GF4 and one hundred nanograms of the indicated activation domain fusion protein encoding plasmids were co-transfected into HT1080 B cells and the transcriptional activity of the GAL4 responsive reporter gene was induced by the addition of indicated concentrations of rapamycin in the medium. In all cases, mean values of SEAP activity secreted into the medium 24 hrs after the addition of rapamycin are shown (+/−S.D.).

FIG. 6A Diagram showing two-hybrid assay using bundled fusion protein containing the target and activation domains. GAL4 DNA binding domain fused to c-Cbl (GCBL) is shown interacting with its target protein SH3 fused to a VP16 activation domain (SH3S).

FIG. 6B Diagram showing two-hybrid assay using bundled fusion protein containing the target and activation domains. GAL4 DNA binding domain fused to c-Cbl (GCBL) is shown interacting with its target protein SH3 fused to a lactose repressor tetramerization domain-VP16 activation domain sequence (SH3MTS).

FIG. 6C HT1080 B cells containing stably integrated GAL4 responsive reporter genes were transfected with 100 ng of indicated expression plasmids. Mean values of SEAP activity secreted into the medium 24 hrs after transfection are shown (+/−S.D.).

FIG. 7 Mutations for the p65 transcription activation domain are listed (SEQ ID Nos 4–21), including:
1. Mutations that are intended to increase activation potency, including M1, M2, M6, M7 and M8.
2. Mutations that are intended to slightly decrease activation potency, including M4 and M5.

DETAILED DESCRIPTION OF THE INVENTION

Definitions

For convenience, the intended meaning of certain terms and phrases used herein are provided below.

"Activate" as applied to the expression or transcription of a gene denotes a directly or indirectly observable increase in the production of a gene product, e.g., an RNA or polypeptide encoded by the gene.

"Capable of selectively hybridizing" means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

"Cells", "host cells" or "recombinant host cells" refer not only to the particular cells under discussion, but also to their progeny or potential progeny. Because certain modifications may occur in succeeding generations due to either mutation or environmental influences, such progeny may not, in fact, be identical to the parent cell, but are still included within the scope of the term as used herein.

"Cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

"Composite", "fusion", and "recombinant" denote a material such as a nucleic acid, nucleic acid sequence or polypeptide which contains at least two constituent portions which are mutually heterologous in the sense that they are not otherwise found directly (covalently) linked in nature, i.e., are not found in the same continuous polypeptide or gene in nature, at least not in the same order or orientation or with the same spacing present in the composite, fusion or recombinant product. Typically, such materials contain components derived from at least two different proteins or genes or from at least two non-adjacent portions of the same protein or gene. In general, "composite" refers to portions of different proteins or nucleic acids which are joined together to form a single functional unit, while "fusion" generally refers to two or more functional units which are linked together. "Recombinant" is generally used in the context of nucleic acids or nucleic acid sequences.

"Cofactor" refers to proteins which either enhance or repress transcription in a nongene specific manner. Cofactors typically lack intrinsic DNA binding specificity, and function as general effectors. Positively acting cofactors do not stimulate basal transcription, but enhance the response to an activator. Positively acting cofactors include PC1, PC2, PC3, PC4, and ACF. TAFs which interact directly with transcriptional activators are also referred to as cofactors.

A "coding sequence" or a sequence which "encodes" a particular polypeptide or RNA, is a nucleic acid sequence which is transcribed (in the case of DNA) and translated (in the case of mRNA) into a polypeptide in vitro or in vivo when placed under the control of an appropriate expression control sequence. The boundaries of the coding sequence are generally determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and synthetic DNA sequences. A transcription termination sequence will usually be located 3' to the coding sequence.

The term "conjoint", with respect to administration of two or more viruses, refers to the simultaneous, sequential or separate dosing of the individual virus. provided that some overlap occurs in the simultaneous presence of the viruses in one or more cells of the animal.

A "construct", e.g., a "nucleic acid construct" or "DNA construct", refers to a nucleic acid or nucleic acid sequence.

"Derived from" denotes a peptide or nucleotide sequence selected from within a given sequence. A peptide or nucleotide sequence derived from a named sequence may further contain a small number of modifications relative to the parent sequence, in most cases representing deletion, replacement or insertion of less than about 15%, preferably less than about 10%, and in many cases less than about 5%, of amino add residues or bases present in the parent sequence. In the case of DNAs, one DNA molecule is also considered to be derived from another if the two are capable of selectively hybridizing to one another. Polypeptides or polypeptide sequences are also considered to be derived from a reference polypeptide or polypeptide sequence if any DNAs encoding the two polypeptides or sequences are capable of selectively hybridizing to one another. Typically, a derived peptide sequence will differ from a parent sequence by the replacement of up to 5 amino acids, in many cases up to 3 amino acids, and very often by 0 or 1 amino acids. A derived nucleic add sequence will differ from a parent sequence by the replacement of up to 15 bases. in many cases up to 9 bases, and very often by 0–3 bases. In some cases the amino acid(s) or base(s) is/are added or deleted rather than replaced.

"Domain" refers to a portion of a protein or polypeptide. In the art, the term "domain" may refer to a portion of a protein having a discrete secondary structure. However, as will be apparent from the context used herein, the term "domain" as used in this document does not necessarily connote a given secondary structure. Rather, a peptide sequence is referred to herein as a "domain" simply to denote a polypeptide sequence from a defined source, or having or conferring an intended or observed activity. Domains can be derived from naturally occurring proteins or may comprise non-naturally-occurring sequence.

"DNA recognition sequence" means a DNA sequence which is capable of binding to one or more DNA-binding domains, e.g., of a transcription factor or an engineered polypeptide.

"Expression control element", or simply "control element", refers to DNA sequences, such as initiation signals, enhancers, promoters and silencers, which induce or control transcription of DNA sequences with which they are operably linked. Control elements of a gene may be located in introns, exons, coding regions, and 3' flanking sequences. Some control elements are "tissue specific", i.e., affect expression of the selected DNA sequence preferentially in specific cells (e.g., cells of a specific tissue), while others are active in many or most cell types. Gene expression occurs preferentially in a specific cell if expression in this cell type is observably higher than expression in other cell types. Control elements include so-called "leaky" promoters, which regulate expression of a selected DNA primarily in one tissue, but cause expression in other tissues as well. Furthermore, a control element can act constitutively or inducibly. An inducible promoter, for example, is demonstrably more active in response to a stimulus than in the absence of that stimulus. A stimulus can comprise a hormone, cytokine, heavy metal, phorbol ester, cyclic AMP (cAMP), retinoic acid or derivative thereof, etc. A nucleotide sequence containing one or more expression control elements may be referred to as an "expression control sequence".

"Gene" refers to a nucleic acid molecule or sequence comprising an open reading frame and including at least one exon and (optionally) one or more intron sequences.

"Genetically engineered cells" denotes cells which have been modified by the introduction of recombinant or heterologous nucleic acids (e.g. one or more DNA constructs or their RNA counterparts) and further includes the progeny of such cells which retain part or all of such genetic modification.

"Keterologous", as it relates to nucleic acid or peptide sequences, denotes sequences that are not normally joined together, and/or are not normally associated with a particular cell. Thus, a "heterologous" region of a nucleic acid construct is a segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, in the case of a cell transduced with a nucleic add construct which is not normally present in the cell, the cell and the construct would be considered mutually heterologous for purposes of this invention. Allelic variation or naturally occurring mutational events do not give rise to heterologous DNA, as used herein.

"Initiator" refers to a short, weakly conserved element that encompasses the transcription start site and which is important for directing the synthesis of properly initiated transcripts.

"Interact" refers to directly or indirectly detectable interactions between molecules, such as can be detected using, for example, a yeast two hybrid assay or by immunoprecipitation. The term "interact" encompasses "binding" interactions between molecules. Interactions may be, for example, protein-protein, protein-nucleic acid, protein-small molecule or small molecule-nucleic acid in nature. "Minimal promoter" refers to the minimal expression control element that is capable of initiating transcription of a selected DNA sequence to which it is operably linked. A minimal promoter frequently consists of a TATA box or TATA-like box. Numerous minimal promoter sequences are known in the literature.

"Nucleic acid" refers to polynucleotides such as deoxyribonucleic acid (DNA), and, where appropriate, ribonucleic acid (RNA). The term should also be understood to include derivatives, variants and analogs of either RNA or DNA made from nucleotide analogs, and, as applicable to the embodiment being described, single (sense or antisense) and double-stranded polynucleotides.

"Operably linked" when referring to an expression control element and a coding sequence means that the expression control element is associated with the coding sequence in such a manner as to permit or facilitate transcription of the coding sequence.

A "recombinant virus" is a virus particle in which the packaged nucleic acid contains a heterologous portion.

"Protein", "polypeptide" and "peptide" are used interchangeably.

A "target gene" is a nucleic acid of interest, the expression of which is modulated according to the methods of the invention. The target gene can be endogenous or exogenous and can integrate into a cell's genome, or remain episomal. The target gene can encode, for instance, a protein, an antisense RNA or a ribozyme.

The terms "transcriptional activation unit" and "activation unit", refer to a peptide sequence which is capable of inducing or otherwise potentiating transcription activator-dependent transcription, either on its own or when linked covalently or non-covalently to another transcriptional activation unit An activation unit may contain a minimal polypeptide sequence which retains the ability to interact directly or indirectly with a transcription factor. Unless otherwise dear from the context, where a fusion protein is referred to as "including" or "comprising" an activation unit, it will be understood that other portions of the protein from which the activation unit is derived can be included. Transcriptional activation units can be rich in certain amino acids. For example, a transcriptional activation unit can be a peptide rich in acidic residues, glutamine, proline, or serine and threonine residues. Other transcriptional activators can be rich in isoleucine or basic amino acid residues (see, e.g., Triezenberg (1995) Cur. Opin. Gen. Develop. 5:190, and references cited therein). For instance, an activation unit can be a peptide motif of at least about 6 amino acid residues associated with a transcription activation domain, including the well-known "acidic", "glutamine-rich" and "proline-rich" motifs such as the K13 motif from p65, the OCT2 Q domain and the OCT2 P domain, respectively.

The term "transcriptional activator" refers to a protein or protein complex, the presence of which can increase the level of gene transcription in a cell of a responsive gene. It is thought that a transcriptional activator is capable of enhancing the efficiency with which the basal transcription complex performs, i.e., activating transcription. Thus, as used herein, a transcriptional activator can be a single protein or alternatively it can be composed of several units at least some of which are not covalently linked to each other. A transcriptional activator typically has a modular structure, i.e., comprises one or more component domains, such as a DNA binding domain and one or more transcriptional activation units or domains. Transcriptional activators are a subset of transcription factors, defined below.

"Transcription factor" refers to any protein whose presence or absence contributes to the initiation of transcription but which is not itself a part of the polymerase. Certain transcription factors stimulate transcription ("transcriptional activators"); other repress transcription ("transcriptional repressors"). Transcription factors are generally classifiable into two groups: (i) the general transcription factors, and (ii) the transcription activators. Transcription factors usually contain one or more regulatory domains. Some transcription factors contain a DNA binding domain, which is that part of the transcription factor which directly interacts with the expression control element of the target gene.

"Transcription regulatory domain" denotes any domain which regulates transcription, and includes activation, synergizing and repression domains. The term "activation domain" denotes a domain, e.g. in a transcription factor, which positively regulates (increases) the rate of gene transcription. The term "repression domain" denotes a domain which negatively regulates (inhibits or decreases) the rate of gene transcription.

A "transcription synergizing domain" is defined as any domain which increases the potency of transcriptional activation when present along with the transcription activation domain. A synergizing domain can be an independent transcriptional activator, or alternatively, a domain which on its own does not induce (or does not usually induce) transcription but is able to potentiate the activity of a transcription activation domain. The synergizing domain can be a component domain of a fusion protein containing the activation domain or can be recruited to the DNA binding domain or other component of the transcription complex, e.g., via a bundling interaction.

"Transfection" means the introduction of a naked nucleic add molecule into a recipient cell. "Infection" refers to the process wherein a nucleic acid is introduced into a cell by a virus containing that nucleic add. A "productive infection" refers to the process wherein a virus enters the cell, is replicated, and is then released from the cell (sometimes referred to as a "lytic" infection). "Transduction" encompasses the introduction of nucleic acid into cells by any means.

"Transgene" refers to a nucleic acid sequence which has been introduced into a cell. Daughter cells deriving from a cell in which a transgene has been introduced are also said to contain the transgene (unless it has been deleted). The polypeptide or RNA encoded by a transgene may be partly or entirely heterologous, i.e., foreign, with respect to the animal or cell into which it is introduced. Alternatively, the transgene can be homologous to an endogenous gene of the transgenic animal or cell into which it is introduced, but is designed to be inserted, or is inserted, into the animal's genome in such a way as to alter the genome of the cell into which it is inserted (e.g., it is inserted at a location which differs from that of the natural gene). A transgene can also be present in an episome. A transgene can include one or more expression control elements and any other nucleic acid, (e.g. intron), that may be necessary or desirable for optimal expression of a selected coding sequence.

The term "vector" refers to a nucleic acid molecule capable of transporting another nucleic acid to which it has been linked. One type of vector is an episome, i.e., a nucleic acid capable of extra-chromosomal replication. Often vectors are used which are capable of autonomous replication and/or expression of nucleic acids to which they are linked. Vectors capable of directing the expression of an included gene operatively linked to an expression control sequence can be referred to as "expression vectors". Expression vectors are typically in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of vectors which serve equivalent functions and which are or become known in the art. Viral vectors are nucleic acid molecules containing viral sequences which can be packaged into viral partides.

Bundling Domains

As described above, bundling domains interact with like domains via protein-protein interactions to induce formation of protein "bundles". Various order oligomers (dimers, trimers, tetramers, etc.) of proteins containing a bundling domain can be formed, depending on the choice of bundling domain.

One example of a dimeriation domain is the leucine zipper (LZ) element. Leucine zippers have been identified, generally, as stretches of about 35 amino acids containing 4–5 leucine residues separated from each other by six amino acids (Maniatis and Abel (1989) Nature 341:24–25). Exemplary leucine zippers occur in a variety of eukaryotic DNA binding proteins, such as GCN4, C/EBP, c-Fos, c-Jun, c-Myc and c-Max. Other dimerization domains include helix-loop-helix domains (Murre, C. et al. (1989) Cell 58:537–544). Dimerization domains may also be selected from other proteins, such as the retinoic acid receptor, the thyroid hormone receptor or other nuclear hormone receptors (Kurokawa et al. (1993) Genes Dev. 7:1423–1435) or from the yeast transcription factors GAL4 and HAP1 (Marmonstein et al. (1992) Nature 356:408–414; Zhang et al. (1993) Proc. Natl. Acad. Sci. USA 90:2851–2855). Dimerization domains are further described in U.S. Pat. No. 5,624,818 by Eisenman.

Of particular current interest are tetramer-forming bundling domains. Incorporation of such a tetramerization domain within a fusion protein leads to the constitutive assembly of tetrameric clusters or bundles. For example, a bundle of four activation units can be assembled by covalently linking the activation unit to a tetramerization domain. By clustering the activation units together through a bundling domain. four activation units can be delivered to a single DNA binding domain at the promoter. The E. coli lactose repressor tetramerization domain (amino acids 46–360; Chakerian et al. (1991) J. Biol. Chem. 266:1371; Alberti et al. (1993) EMBO J. 12:3227; and Lewis et al. (1996) Nature 271:1247), illustrates this class. Furthermore, since the fusion proteins may contain more than one activation unit linked to the bundling domain, each of the four proteins of the tetramer can contain more than one activation unit (and the complex may comprise more than 4 activation units).

Other illustrative tetramerization domains include those derived from residues 322–355 of p53 (Wang et al. (1994) Mol. Cell. Biol. 14:5182; Clore et al. (1994) Science 265:386) see also U.S. Pat. No. 5,573,925 by Halazonetis. Other bundling domains can be derived from the Dimerization cofactor of hepatocyte nuclear factor-1 (DCoH). DCoH associates with specific DNA binding proteins and also catalyses the dehydration of the biopterin cofactor of phenylalanine hydroxylase. DCoH is a tetramer. See e.g. Endrizzi, J. A., Cronk, J. D., Wang, W., Crabtree, G. R and Alber, T. (1995) Science 268, 556559; Suck and Ficner (1996) FEBS Lett 389(1):3–39; Standmann, Senkel and Ryffel (1 998) Int J Dev Biol 42(1):53–59

The bundling domain may comprise a naturally-occurring peptide sequence or a modified or artificial peptide sequence. Sequence modifications in the bundling domain may be used to increase the stability of bundle formation or to help avoid unintended bundling with native protein molecules in the engineered cells which contain a wild-type bundling domain.

For example, sequence substitutions that stabilize oligomerization driven by leucine zippers are known (Krylov et al. (1994) cited above; O'Shea et al. (1992) cited above). To illustrate, residues 174 or 175 of human p53 may be replaced by glutamine or leucine, respectively.

To illustrate sequence modifications aimed at avoiding unintended bundling with endogenous protein molecules, the p53 tetramerization domain may be modified to reduce the likelihood of bundling with endogenous p53 proteins that have a wild-type p53 tetramerization domain, such as wild-type p53 or tumor-derived p53 mutants. Such altered p53 tetramerization domains are described in U.S. Pat. No. 5,573,925 by Halazonetis and are characterized by disruption of the native p53 tetramerization domain and insertion of a heterologous bundling domain in a way that preserves tetramerization. Disruption of the p53 tetramerization domain involving residues 335–348, or a subset of these residues, sufficiently disrupts the function of this domain so that it can no longer drive tetramerization with wild-type p53 or tumor-derived p53 mutants. At the same time, however, introduction of a heterologous dimerization domain reestablishes the ability to form tetramers, which is mediated both by the heterologous dimerization domain and by the residual portion of the p53 tetramerization domain sequence.

Other suitable bundling domains can be readily selected or designed by the practitioner, including semi-artificial bundling domains, such as variants of the GCN4 leucine zipper that form tetramers (Alberti et al. (1993) EMBO J. 12:3227–3236; Harbury et al. (1993) Science 262:1401–1407; Krylov et al. (1994) (1994) EMBO J. 13:2849–2861). The tetrameric variant of GCN4 leucine zipper described in Harbury et al. (1993), supra, has isoleucines at positions d of the coiled coil and leucines at positions a, in contrast to the original zipper which has leucines and valines, respectively.

The choice of bundling domain can be based, at least in part, on the desired conformation of the bundles. For instance, the GCN4 leucine zipper drives parallel subunit assembly [Harbury et al. (1993), cited above], while the native p53 tetramerization domain drives antiparallel assembly [Clore et al. (1994) cited above; Sakamoto et al. (1994) Proc. Natl. Acad. Sci. USA 91:8974–8978].

In addition, a variety of techniques are available for identifying other naturally occurring bundling domains, as well as for selecting bundling domains derived from mutant or otherwise artificial sequences. See, for example, Zeng et al. (1997) Gene 185:245; O'Shea et al. (1992) Cell 68:699–708; Krylov et al. [cited above].

In applications of the invention involving the genetic engineering of cells within (or for use within) whole animals, the use of peptide sequence derived from that species is preferred when possible. For instance, for applications involving human gene therapy, use of bundling domains derived from human proteins may minimize the risk of immunogenic reactions. However, in some cases the use of bundling domains of human origin may induce interactions between the fusion proteins and the endogenous protein from which the bundling domain was derived, i.e., leading to unwanted bundling of fusion proteins with the endogenous protein containing the identical bundling domain. Such interactions, in addition to inhibiting target gene expression, may also have other adverse effects in the cell, e.g., by interfering with the function of the endogenous protein from which the bundling domain was derived.

Approaches for avoiding unwanted bundling of fusion proteins of this invention with endogenous proteins include using a bundling domain which is (a) heterologous to the host organism, (b) expressed by the host organism but only (or predominantly) in cells or tissues other than those which will express the fusion proteins, or (c) engineered through modification in peptide sequence such that it bundles preferentially with itself rather than with an endogenous bundling domain.

The first approach is illustrated by the use of a bacterial lac repressor tetramerization domain in human cells.

The second approach requires the use of a bundling domain derived from a protein which is not expressed in the cells or tissues which are to be engineered to express the fusion protein(s) of this invention, at least not at a level which would cause undue interference with the bundling application or with normal cell function. Fusion proteins containing a bundling domain derived from an endogenous protein expressed selectively or preferentially in one tissue could be expressed in a different tissue without any adverse effects. For example, to regulate gene expression in human muscle, fusion proteins containing bundling domains from a protein expressed in liver, brain or some other tissue or tissue—but not in muscle—can be expressed in muscle cells without undue risk of mismatched bundling.

In the third approach, and as noted previously, the binding specificity of the bundling domain is engineered by alterations in peptide sequence to replace (in whole or part) bundling activity for proteins containing the wild-type bundling domain with bundling activity for proteins containing the modified peptide sequence.

Several examples of tissue-specific bundling domains which could be used in the practice of this invention include bundling domains derived from the Retinoid X receptor, (Kersten, S., Reczek, P. R and N. Noy (1997) J. Biol. Chem. 272, 29759–29768); Dopamine D3 receptor (Nimchinsky, E. A., Hof, P. R., Janssen, W. G. M., Morrison, J. H and C. Schmauss (1997) J. Biol. Chem. 272, 29229–29237); Butyrylcholinesterase (Blong, R. M., Bedows, E and O. Lockridge (1997) Biochem. J. 327, 747–757); Tyrosine Hydroxylase (Goodwill, K. E., Sabatier, C., Marks, C., Raag, R., Fitzpatrick, P. F and R. C. Stevens (1997) Nat. Struct. Biol 7, 578–585). Bcr (McWhirter, J. R., Galasso, D. L and J. Y. Wang (1993) Mol. Cell. Biol. 13, 7587–7595); and Apolipoprotein E (Westerlund, J. A and K. H. Weisgraber (1993) J. Biol. Chem. 268,15745–15750).

Transcription Activation Domains/Activation Units

Transcription activation domains and activation units can comprise naturally-occurring or non-naturally occurring peptide sequence so long as they are capable of activating or potentiating transcription of a target gene construct. A variety of polypeptides and polypeptide sequences which can activate or potentiate transcription in eukaryotic cells are known and in many cases have been shown to retain their activation function when expressed as a component of a fusion protein. An activation unit is generally at least 6 amino acids, and preferably contains no more than about 300 amino acid residues, more preferably less than 200, or even less than 100 residues.

Naturally occurring activation units include portions of transcription factors, such as a thirty amino acid sequence from the C-terminus of VP16 (amino acids 461–490), referred to herein as "Vc". Other activation units are derived from naturally occurring peptides. For example, the replacement of one amino acid of a naturally occurring activation unit by another may further increase activation. An example of such an activation unit is a derivative of an eight amino acid peptide of VP16, the derivative having the amino acid sequence DFDLDMLG (SEQ ID NO:1. Other activation units are "synthetic" or "artificial" in that they are not derived from a naturally occurring sequence. It is known, for example, that certain random alignments of acidic amino acids are capable of activating transcription.

Certain transcription factors are known to be active only in specific cell types, i.e., they activate transcription in a tissue specific manner. By using activation units which function selectively or preferentially in specific cells, it is possible to design a transcriptional activator of the invention having a desired tissue specificity.

One source of peptide sequence for use in a fusion protein of this invention is the herpes simplex virus virion protein 16 (referred to herein as VP16, the amino acid sequence of which is disclosed in Triezenberg, S. J. et al. (1988) Genes Dev. 2:718–729). For example, an activation unit corresponding to about 127 of the C-terminal amino acids of VP16 can be used. Alternatively, at least one copy of about 11 amino acids from the C-terminal region of VP16 which retains transcription activation ability is used as an activation unit Preferably, an oligomer comprising two or more copies of this sequence is used. Suitable C-terminal peptide portions of VP16 include those described in Seipel, K. et al. (EMBO J. (1992) 13:4961–4968).

Another example of an acidic activation unit is provided in residues 753–881 of GAL4.

One particularly important source of transcription activation units is the (human) NF-kB subunit p65. The activation domain may contain one or more copies of a peptide sequence comprising all or part of the p65 sequence spanning residues 450–550, or a peptide sequence derived therefrom. In certain embodiments, it has been found that extending the p65 peptide sequence to include sequence spanning p65 residues 361–450, e.g., including the "AP activation unit", leads to an unexpected increase in transcription activation. Moreover, a peptide sequence comprising all or a portion of p65(361–550), or peptide sequence derived therefrom, in combination with heterologous activation units, can yield surprising additional increases in the level of transcription activation. p65-based activation domains function across a broad range of promoters and in a number of bundling experiments have yielded increases in transcription levels of chromosomally incorporated target genes six-fold, eight-fold and even 14–15-fold higher than obtained with unbundled tandem copies of VP16 which itself is widely recognized as a very potent activation domain.

It is expected that recombinant DNA molecules encoding fusion proteins which contain a p65 activation unit, or peptide sequence derived therefrom, will provide significant advantages for heterologous gene expression in its various contexts, including dimerization based regulated systems such as described in International patent applications PCT/US94/01617, PCT/US95110591, PCT/US96/09948 and the like, as well as in other heterologous transcription systems including allostery-based regulation such as those involving tetracycline-based regulation reported by Bujard et al. and those involving steroid or other hormone-based regulation.

One class of p65-based transcription factors contain more than one copy of a p65-derived domain. Such proteins will typically contain two or more, generally up to about six, copies of a peptide sequence comprising all or a portion of p65(361–550), or peptide sequence derived therefrom. Such iterated p65-based transcription activation domains are useful both in bundled and non-bundled approaches.

Other polypeptides with transcription activation activity in eukaryotic cells can be used to provide activation units for the fusion proteins of this invention. Transcription activation domains found within various proteins have been grouped into categories based upon shared structural features. Types of transcription activation domains include acidic transcription activation domains (noted previously), proline-rich transcription activation domains, serine/threonine-rich transcription activation domains and glutamine-rich transcription activation domains. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcription activation domains, are disclosed in Seipel, K. et al. (EMBO J. (1992) 13:4961–4968).

Still other illustrative activation domains and motifs of human origin include the activation domain of human CTF, the 18 amino acid (NFLQLPQQTQGALLTSPQ) (SEQ ID NO:2) glutamine rich region of Oct-2, the N-terminal 72 amino acids of p53, the SYGQQS (SEQ ID NO:3) repeat 2 in Ewing sarcoma gene and an 11 amino acid (535–545) acidic rich region of Rel A protein.

In addition to previously described transcription activation domains, novel transcription activation units, which can be identified by standard techniques, are within the scope of the invention. The transcription activation ability of a polypeptide can be assayed by linking the polypeptide to a DNA binding domainand determining the amount of transcription of a target sequence that is stimulated by the fusion protein. For example, a standard assay used in the art utilizes a fusion protein of a putative activation unit and a GAL4 DNA binding domain (e.g., amino acid residues 1–93). This fusion protein is then used to stimulate expression of a reporter gene linked to GAL4 binding sites (see e.g., Seipel, K. et al. (1992) EMBO J. 11:4961–4968 and references cited therein).

The activation domains of the invention can be from any eukaryotic species (including but not limited to various yeast species and various vertebrate species, including the mammals), and it is not necessary that every activation unit or domain be from the same species. In applications of this invention to whole organisms, it is often preferable to use activation units and activation domains from the same species as the recipient to avoid immune reactions against the fusion proteins.

Mutations in the Activation Domain

One way to increase the potency of an activation domain is to increase its acidic or hydrophobic content through modifications in peptide sequence. Acidic amino acids which can increase potency of activation domains include aspartic acid and glutamic acid. In some cases, one may want to decrease (usually only modestly) the potency of the activation domain in order to obtain a less steep activation curve, especially if a greater number of individually weaker activation domains will be deployed together, e.g., by bundling.

Thus, in one embodiment of this invention, mutations are introduced into the activation domain by standard techniques known in the art, such as site-directed PCR based mutagenesis. In this embodiment, one to five, in some cases one to three, alterations in peptide sequence can be introduced into the DNA coding for the activation domain. Each of these mutations either alone or in combination with one or more other mutations may be readily assayed for its ability to induce the transcription of either transiently transfected or stably integrated target reporter gene constructs. For instance, a construct encoding a fusion protein containing multiple copies of the modified sequence and a DNA binding domain can be introduced into cells and the activity of the encoded fusion protein measured in transcription assays (with a responsive reporter gene construct) and compared to analogous fusion proteins containing wild-type activation domain sequence or a different mutation of interest.

The foregoing is illustrated in the case of the p65 transcription activation domains. Constructs are prepared encoding fusion proteins containing one or more p65 transcription activation domains and a DNA binding domain. The p65 domains may be wild-type (as a control) or may contain any of a variety of alterations in peptide sequence. These mutations can generally be introduced into a variety of p65-derived transcription activation domains. For example, M1 mutations can be introduced into plasmids carrying p65 activation domain coding regions between amino acids 533 and 550, or 361 and 550, or 280 and 550.

Exemplary mutations for p65 transcription activation domains include those intended to increase the potency of the p65 activation domain (including the M1, M2, M6, M7 and M8 mutations) and those intended to decrease the potency (generally slightly) of the activation domain. The p65 activation domain contains four phenylalanine residues and mutations that convert these residues to alanine has been shown to significantly reduce the potency of the p65 activation domain in yeast and in vitro experiments. Our experiments show that changing F 533 and F 541 to alanine residues reduced the potency of p65 activation domain in to half of wild type level. Mutations of the M4 and M5 class change the conserved serine and proline residues between amino-acids 361 and 450. Our data show that M4 and M5 mutant sequences can induce the expression of target genes synergistically when fused to other acidic type activation domains. In GST pull down assays, the region of the M4 and M5 mutations interacts with TFIIA. Although M4 and MS mutations individually have a very small effect on the ability of p65 activation domain to induce the reporter gene, combined together, they significantly reduce its potency. Thus, mutations for the practitioner to bear in mind include, but are not limited to, the following:

WT: 532-DFSSIADMDFSALLSQIS (SEQ ID NO:4)
M1: 532-DFSDFADMDFDADLSQIS (SEQ ID NO:5)
WT: 439-ALLQLQFDDED (SEQ ID NO:6)
M2: 439-ALLDLDFDDED (SEQ ID NO:7)

WT: 529-GDEDFSSIADMDFSALLSQI (SEQ ID NO:8)
M3: 529-GDEDASSIADMDASALLSQI (SEQ ID NO:9)
WT: 377-SALALPAPPQVL (SEQ ID NO:10)
M4: 377-GALALGAGGQVL(SEQ ID NO:11)
WT: 401-SALAQAPAPVP (SEQ ID NO:12)
M5: 401-GALAQAGAGVG (SEQ ID NO:13)
WT: 434-GTLSEALLQLQFD (SEQ ID NO:14)
M6: 434-GDFS-ALLQLQFD (SEQ ID NO:15)
WT: 472-SEFQQLLNQ (SEQ ID NO:16)
M7: 472-SEFSALLNQ (SEQ ID NO:17)
WT: 472-SEFQQLLNQ (SEQ ID NO:18)
M8: 472-SDFQQLLNQ (SEQ ID NO:19)
WT: 530-DEDFSSIADMDFS (SEQ ID NO:20)
M9:530-DEDFSSLLDMDFS (SEQ ID NO:21)

Synergizing Domains

A synergizing domain is any domain which observably increases the potency of transcription activation when recruited to the promoter along with the transcription activation domain. A synergizing domain can be an independent transcription activation domain or an activation unit which on its own does not induce transcription but is able to potentiate the activity of a transcription activation domain with which it is linked covalently (i.e., within the same fusion protein) or with which it is associated non-covalently (e.g., through bundling or ligand-mediated clustering).

One example of a synergizing domain is the so-called "alanine/proline rich" or "AP" activation motif of p65, which extends from about amino acids 361 to about amino acid 450 of that protein. Similar AP activation motifs are also present in, e.g., the p53 and CTF proteins. The presence of one or several copies of an AP domain alone in a protein does not itself provide the ability to induce activator-dependent transcription activation. However, when linked to activation units which are themselves capable of inducing some level of activator-dependent transcription, e.g., another portion of p65 or VP16, the AP activation unit synergizes with the second activation domain to induce an increase in the level of transcription.

Accordingly,. the invention provides an AP activation unit, functional derivative thereof, or other synergizing domain which on its own is incapable of activating transcription. Functional alternative sequences for use as synergizing domains, including among others derivatives of an AP activation unit, can be obtained, for instance, by screening candidate sequences for binding to TFIIA and measuring transcriptional activity in a co-transfection assay. Such equivalents are expected to include forms of the activation unit which are truncated at either the N-terminus or C-terminus or both, e.g., fragments of p65 (or homologous sequences thereto) which are about 75, 60, 50, 30 or even 20 amino acid residues in length (e.g., ranging in length from 20–89 amino acids). Likewise, it is expected that the AP activation unit sequence from p65 can tolerate amino acid substitutions, e.g., to produce AP motifs of at least 95%, 90%, 80% and even 70% identity with the AP activation unit sequence of SEQ ID No. 2 of U.S. Ser. No. 08/918,401. These and other AP derivatives include, for example, AP domains based on naturally-occurring sequence but modified by the replacement, insertion or deletion of 1, 2, 3, 4 or 5 amino acid residues.

Other synergizing domains are independent activation domains, e.g. VP16. While VP16 can activate transcription on its own, it can synergize with p65 to produce levels of transcription that are greater than the sum of the transcription levels effected by each activation domain alone. As shown in the examples, fusion of VP16 to a nucleic acid containing an FRB domain, a lac repressor tetramerization domain and p65 greatly increases the level of expression of a target gene as compared to the same construct in the absence of VP16.

Synergizing domains may also be fused to an unbundled or bundled DNA binding domain. To avoid the activation of transcription in a constitutive manner with constructs such as these, it is preferable that the synergizing domain itself be incapable of activating transcription.

Ligand Binding Domains

Fusion proteins containing a ligand binding domain for use in practicing this invention can function through one of a variety of molecular mechanisms.

In certain embodiments, the ligand binding domain permits ligand-mediated cross-linking of the fusion protein molecules bearing appropriate ligand binding domains. In these cases, the ligand is at least divalent and functions as a dimerizing agent by binding to the two fusion proteins and forming a cross-linked heterodimeric complex which activates target gene expression. See e.g. WO 94/18317, WO 96/20951, WO 96/06097, WO 97/31898 and WO 96/41865.

In other embodiments, the binding of ligand to fusion protein is thought to result in an allosteric change in the protein leading to the binding of the fusion protein to a target DNA sequence [see e.g. U.S. Pat. Nos. 5,654,168 and 5,650,298 (tet systems), and WO 93/23431 and WO 98/18925 (RU486-based systems)] or to another protein which binds to the target DNA sequence [see e.g. WO 96/37609 and WO 97/38117 (eodysone/RXR-based systems)], in either case, modulating target gene expression.

Dimerization-based Systems

In the cross-linking-based dimerization systems the fusion proteins can contain one or more ligand binding domains (in some cases containing two, three or four such domains) and can further contain one or more additional domains, heterologous with respect to the ligand binding domain, including e.g. a DNA binding domain, transcription activation domain, etc.

In general, any ligand/ligand binding domain pair may be used in such systems. For example, ligand binding domains may be derived from an immunophilin such as an FKBP, cyclophilin, FRB domain, hormone receptor protein, antibody, etc., so long as a ligand is known or can be identified for the ligand binding domain.

For the most part, the receptor domains will be at least about 50 amino acids, and fewer than about 350 amino acids, usually fewer than 200 amino acids, either as the natural domain or truncated active portion thereof. Preferably the binding domain will be small (<25 kDa, to allow efficient transfection in viral vectors), monomeric, nonimmunogenic, and should have synthetically accessible, cell perneant, nontoxic ligands as described above.

Preferably the ligand binding domain is for (i.e., binds to) a ligand which is not itself a gene product (i.e., is not a protein), has a molecular weight of less than about 5 kD and preferably less than about 2.5 kD, and is cell permeant. In many cases it will be preferred that the ligand does not have an intrinsic pharmacologic activity or toxicity which interferes with its use as a transcription regulator.

The DNA sequence encoding the ligand binding domain can be subjected to mutagenesis for a variety of reasons. The mutagenized ligand binding domain can provide for higher binding affinity, allow for discrimination by a ligand between the mutant and naturally occurring forms of the ligand binding domain, provide opportunities to design ligand-ligand binding domain pairs, or the like. The change in the ligand binding domain can involve directed changes in amino acids known to be involved in ligand binding or with ligand-dependent conformational changes. Alternatively, one may employ random mutagenesis using combinatorial techniques. In either event, the mutant ligand binding domain can be expressed in an appropriate prokaryotic or eukarotic host and then screened for desired ligand binding or conformational properties. Examples involving FKBP, cyclophilin and FRB domains are disclosed in detail in WO 94/18317, WO 96/06097, WO 97/31898 and WO 96/41865. For instance, one can change Phe36 to Ala and/or Asp37 to Gly or Ala in FKBP12 to accommodate a substituent at positions 9 or 10 of the ligand FK506 or FK520 or analogs, mimics, dimers or other derivatives thereof. In particular, mutant FKBP12 domains which contain Val, Ala, Gly, Met or other small amino acids in place of one or more of Ty26, Phe36, Asp37, Tyr82 and Phe99 are of particular interest as receptor domains for FK506-type and FK-520-type ligands containing modifications at C9 and/or C10 and their synthetic counterparts (see e.g., WO 97/31898). Illustrative mutations of current interest in FKBP domains also include the following:

TABLE 1

| | | | |
|---|---|---|---|
| F36A | Y26V | F46A | W59A |
| F36V | Y26S | F48H | H87W |
| F36M | D37A | F48L | H87R |
| F36S | I90A | F48A | F36V/F99A |
| F99A | I91A | E54A/F36V/F99G | F99G |
| F46H | E54K/F36M/F99A | Y26A | F46L |
| V55A | F36M/F99G | | |

Entries identify the native amino acid by single letter code and sequence position, followed by the replacement amino acid in the mutant.
Thus, F36V designates a human FKBP12 sequence in which phenylalanine at position 36 is replaced by valine.
F36V/F99A indicates a double mutation in which phenylalanine at positions 36 and 99 are replaced by valine and alanine, respectively.

Illustrative examples of domains which bind to the FKBP:rapamycin complex ("FRBs") are those which include an approximately 89-amino acid sequence containing residues 2025–2113 of human FRAP. Another FRAP-derived sequence of interest comprises a 93 amino acid sequence consisting of amino acids 2024–2113. Similar considerations apply to the generation of mutant FRAP-derived domains which bind preferentially to FKBP complexes with rapamycin analogs (rapalogs) containing modifications (i.e., are "bumped") relative to rapamycin in the FRAPbinding portion of the drug. For example, one may obtain preferential binding using rapalogs bearing substituents other than—OMe at the C7 position with FRBs based on the human FRAP FRB peptide sequence but bearing amino acid substitutions for one of more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, T2098L, and T2098S. Rapalogs bearing substituents other than —OH at C28 and/or substituents other than =O at C30 may be used to obtain preferential binding to FRAP proteins bearing an amino acid substitution for Glu2032. Exemplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the procedures described above to identify mutant FRAPs that bind preferentially to bumped rapalogs.

Other macrolide binding domains useful in the present invention, including mutants thereof, are described in the art. See, for example, WO96/41865, WO96/13613, WO96/06111, WO96/06110, WO96/06097, WO96/12796, WO95/05389, WO95/02684, WO94/18317.

The ability to employ in vitro mutagenesis or combinatorial modifications of sequences encoding proteins allows for the production of libraries of proteins which can be screened for binding affinity for different ligands. For example, one can randomize a sequence of 1 to 5, 5 to 10, or 10 or more codons, at one or more sites in a DNA sequence encoding a binding protein, make an expression construct and introduce the expression construct into a unicellular microorganism, and develop a library of modified sequences. One can then screen the library for binding affinity of the encoded polypeptides to one or more ligands. The best affinity sequences which are compatible with the cells into which they would be introduced can then be used as the ligand binding domain for a given ligand. The ligand may be evaluated with the desired host cells to determine the level of binding of the ligand to endogenous proteins. A binding profile may be determined for each such ligand which compares ligand binding affinity for the modified ligand binding domain to the affinity for endogenous proteins. Those ligands which have the best binding profile could then be used as the ligand. Phage display techniques, as a non-limiting example, can be used in carrying out the foregoing.

In other embodiments, antibody subunits, e.g. heavy or light chain, particularly fragments, more particularly all or part of the variable region, or single chain antibodies, can be used as the ligand binding domain. Antibodies can be prepared against haptens which are pharmaceutically acceptable and the individual antibody subunits screened for binding affinity. cDNA encoding the antibody subunits can be isolated and modified by deletion of the constant region, portions of the variable region, mutagenesis of the variable region, or the like, to obtain a binding protein domain that has the appropriate affinity for the ligand. In this way, almost any physiologically acceptable hapten can be employed as the ligand. Instead of antibody units, natural receptors can be employed, especially where the binding domain is known. In some embodiments of the invention, a fusion protein comprises more than one ligand binding domain. For example, a DNA binding domain can be linked to 2, 3 or 4 or more ligand binding domains. The presence of multiple ligand binding domains means that ligand-mediated cross-linking can recruit multiple fusion proteins containing transcription activation domains to the DNA binding domain-containing fusion protein.

Allostery-based Systems

As mentioned previously, systems for transcription regulation based on ligand-dependent allosteric changes in a chimeric transcription factor are also useful in practicing the subject invention. One such system employs a deletion mutant of the human progesterone receptor which no longer binds progesterone or other endogenous steroids but can be activated by the orally active progesterone antagonist RU486, described, e.g., in Wang et al. (1994) Proc. Natl. Acad. Sci. U.S.A. 91:8180. Activation was demonstrated in cells transplanted into mice using doses of RU486 (5–50 g/kg) considerably below the usual dose for inducing abortion in humans (10 mg/kg). However, the reported induction ratio in culture and in animals was rather low.

Another such system is the ecdysone inducible system. Early work demonstrated that fusing the Drosophila steroid ecdysone (Ec) receptor (EcR) Ec- binding domain to heterologous DNA binding and activation domains, such as *E. coli* lexA and herpesvirus VP16 permits ecdysone-dependent activation of target genes downstream of appropriate binding sites (Christopherson et al. (1992) Proc. Natl. Acad. Sci. U.S.A. 89:6314). An improved ecdysone regulation system has been developed, using the DNA binding domain of the EcR itself. In this system, the regulating transcription factor is provided as two proteins: (1) a truncated, mutant EcR fused to herpes VP16 and (2) the mammalian homolog (RXR) of Ultraspiracle protein (USP), which heterodimerizes with the EcR (No et al. (1996) Proc. Natl. Acad. Sci. U.S.A. 93:3346). In this system, because the DNA binding domain was also recognized by a human receptor (the human famesoid X receptor), it was altered to a site recognized only by the mutant EcR. Thus, the invention provides an ecdysone inducible system, in which a truncated mutant EcR is fused to at least one subunit of a transcription activator of the invention. The transcription factor further comprises USP, thereby providing high level induction of transcription of a target genehaving the EcR target sequence, dependent on the presence of ecdysone.

In another approach, the inducible system comprises or is derived from the *E. coli* tet repressor (TetR), which binds to tet operator (tetO) sequences upstream of target genes. (n the presence of tetracycline, or a tetracycline analog which bind to tetR, DNA binding is abolished and thus transactivation is abolished. This system, in which the TetR had previously been linked to transcription activation domains, e.g., from VP16, is generally referred to as an allosteric "off-switch" described by Gossen and Bujard (Proc. Natl. Acad. Sci. U.S.A. (1992) 89:5547) and in U.S. Pat. Nos. 5,464,758; 5,650,298; and 5,589,362 by Bujard et al. Target gene expression is reportedly regulatable over several orders of magnitude in a reversible manner. This system is said to provide low background and relatively high target gene expression in the absence of tetracycline or an analog. The invention described herein provides a method for obtaining even stronger transcription induction of a target gene, which is regulatable by the tetracycline system or other inducible DNA binding domain.

In some embodiments, a "reverse" Tet system is used, again based on a DNA binding domain that is a mutant of the *E. coli* TetR, but which binds to TetO in the presence of Tet. Additional information on mutated tetR-based systems is provided above and in patent documents cited previously. The use of bundling as described herein provides a method for obtaining even stronger transcription induction of a target gene in the presence of tetracycline or an analog thereof from a very low background in the absence of tetracycline.

A tetR domain useful in the practice of this invention may comprise a naturally occurring peptide sequence of a tetR of any of the various classes (e.g. class A, B, C, D or E) (in which case the absence of the ligand stimulates target gene transcription), or more preferably, comprises a mutated tetR which is derived from a naturally occurring sequence from which it differs by at least one amino acid substitution, addition or deletion. Of particular interest are those mutated tetR domains in which the presence of the ligand stimulates binding to the TetO sequence, usually to induce target gene transcription in a cell engineered in accordance with this invention. For example, mutated tetR domains include mutated Tn10-derived tetR domains having an amino acid substitution at one or more of amino acid positions 71, 95, 101 and 102. By way of further illustration, one mutated tetR comprises amino acids 1–207 of the Tn10 tetR in which glutamic acid 71 is changed to lysine, aspartic acid 95 is changed to asparagine, leucine 101 is changed to serine and glycine 102 is changed to aspartic acid. Ligands include tetracycline and a wide variety of analogs and mimics of tetracycline, including for example, anhydrotetracycline and doxycycline. Target gene constructs in these embodiments contain a target gene operably linked to an expression control sequence including one or more copies of a DNA sequence recognized by the tetR of interest, including for example, an upstream activator sequence for the appropriate tet operator. See e.g. U.S. Pat. No. 5,654,168.

Ligands of the Invention

In various embodiments where a ligand binding domain for the ligand is endogenous to the cells to be engineered, it is often desirable to alter the peptide sequence of the ligand binding domain and to use a ligand which discriminates between the endogenous and engineered ligand binding domains. Such a ligand should bind preferentially to the engineered ligand binding domain relative to a naturally occurring peptide sequence, e.g., from which the modified domain was derived. This approach can avoid untoward intrinsic activities of the ligand. Significant guidance and illustrative examples toward that end are provided in the various references cited herein.

Cross-linking/dimerization Systems

Any ligand for which a binding protein or ligand binding domain is known or can be identified may be used in combination with such a ligand binding domain in carrying out this invention.

Extensive guidance and examples are provided in WO 94/18317 for ligands and other components useful for cross-linked oligomerization-based systems. Systems based on ligands for an immunophilin such as FKBP, a cyclophilin, and/or FRB domain are of special interest. Illustrative examples of ligand binding domain/ligand pairs that may be used for cross-linking include, but are not limited to: FKBP/FK1012, FKBP/synthetic divalent FKBP ligands (see WO 96/06097 and WO 97/31898), FRB/rapamycin or analogs thereof:FKBP (see e.g., WO 93/33052, WO 96/41865 and Rivera et al, "A humanized system for pharmacologic control of gene expression", Nature Medicine 2(9):1028–1032 (1997)), cyclophilin/cyclosporin (see e.g. WO 94/18317), FKBP/FKCsA/cyclophilin (see e.g. Belshaw et al, 1996, PNAS 93:4604–4607), DHFR/methotrexate (see e.g. Licitra et al, 1996, Proc. Natl. Acad. Sci. USA 93:12817–12821), and DNA gyrase/coumermycin (see e.g. Farrar et al, 1996, Nature 383:178–181). Numerous variations and modifications to ligands and ligand binding domains, as well as methodologies for designing, selecting and/or characterizing them, which may be adapted to the present invention are disclosed in the cited references.

Allostery-based Systems

For additional guidance on ligands for other systems which may be adapted to this invention, see e.g. (Gossen and Bujard Proc. Natl. Acad. Sci. U.S.A. 1992 89:5547, and U.S. Pat. Nos. 5,654,168, 5,650,298, 5,589,362 and 5,464,758 (TetR/tetracycline), Wang et al, 1994, Proc. Natl. Acad. Sci. USA 91:8180–8184 (progesterone receptor/RU486), and No et al, 1996, Proc. Natl. Acad. Sci. USA 93:3346–3351 (ecdysone receptor/ecdysone).

DNA-binding Domains

Regulated expression systems relevant to this invention involve the use of a protein containing a DNA binding domain to selectively target a desired gene for expression (or repression). Systems based on ligand-mediated cross-linking generally rely upon a fusion protein containing the DNA binding domain together with one or more ligand binding domains. One general advantage of such systems is that they are particularly modular in nature and lend themselves to a wide variety of design choices. These systems permit wide latitude-in the choice of DNA binding domains. Many allostery-based systems, like the TetR- and progesterone-R-based systems, use a fusion protein containing a DNA binding domain together with a transcription regulatory domain (e.g. a transcription activation or repression domain). Some allostery-based systems such as the ecdysone-regulated system, use a protein like RXR which contains a DNA binding domain together with a binding site for another protein (such as the ecdysone receptor). Of the allostery-based systems, the progesterone receptor-based system and like systems permit relatively greater latitude in the choice of DNA binding domain. While allostery-based systems like the TetR- and ecdysone receptor type may be engineered at the DNA binding domain, they are somewhat less amenable to ready replacement of the DNA binding domain.

Various DNA binding domains may be incorporated into the design of fusion proteins of this invention, especially those of the ligand-mediated cross-linking type and the progesterone-R-based type, so long as a corresponding DNA "recognition" sequence is known, or can be identified, to which the domain is capable of binding. One or more copies of the recognition sequence are incorporated into, or present within, the expression control sequence of the target gene construct. Peptide sequence of human origin is often preferred, where available, for uses in human gene therapy. Composite DNA binding domains provide one means for achieving novel sequence specificity for the protein-DNA binding interaction. An illustrative composite DNA binding domain containing component peptide sequences of human origin is ZFHD-1 which is described in detail below. Individual DNA-binding domains may be further modified by mutagenesis to decrease, increase, or change the recognition specificity of DNA binding. These modifications can be achieved by rational design of substitutions in positions known to contribute to DNA recognition (often based on homology to related proteins for which explicit structural data are available).

For example, in the case of a homeodomain, substitutions can be made in amino acids in the N-terminal arm, first loop, second helix, and third helix known to contact DNA. In zinc fingers, substitutions can be made at selected positions in the DNA recognition helix. Alternatively, random methods, such as selection from a phage display library can be used to identify altered domains with increased affinity or altered specificity.

For additional examples, information and guidance on designing, mutating, selecting, combining and characterizing DNA binding domains, see, e.g., Pomerantz J L, Wolfe S A, Pabo C O, Structure-based design of a dimeric zinc finger protein Biochemistry 1998 Jan 27;37(4):965–970; Kim J-S and Pabo C O, Getting a Handhold on DNA: Design of Poly-Zinc Finger Proteins with Femtomolar Dissociation Constants, PNAS USA, 1998 Mar 17;95(6):2812–2817; Kim J S, Pabo C O, Transcriptional repression by zinc finger peptides. Exploring the potential for applications in gene therapy., J Biol Chem 1997 Nov 21;272(47):29795–29800; Greisman H A, Pabo C O, A general strategy for selecting high-affinity zinc finger proteins for diverse DNA target sites, Science 1997 Jan 31;275(5300):657–661; Rebar E J, Greisman H A, Pabo G O, Phage display methods for selecting zinc finger proteins with novel DNA-binding specificities, Methods Enzymol 1996;267:129–149; Pomerantz J L, Pabo G O, Sharp P A, Analysis of homeodomain function by structure-based design of a transcription factor, Proc Natl Acad Sci USA 1995 Oct 10;92(21):9752–9756; Rebar E J, Pabo C O, Zinc finger phage: affinity selection of fingers with new DNA-binding specificities, Science 1994, Feb 4;263:671–673; Choo Y, Sanches-Garcia I, Klug A, In vivo repression by a site-specific DNA-binding protein designed against an oncogenic sequence, Nature 1994, Dec 15;372:642–645; Choo Y, Klug A, Toward a code for the interaction of zinc fingers with DNA: Selection of randomized fingers displayed on phage, PNAS USA, November 1994; 91:11163–11167; Wu H, Yang W-P, Barbas C F III, Building zinc fingers by selection: toward a therapeutic application, PNAS USA January 1995; 92:344–348; Jamieson A C, Kim S-H, Wells J A, In Vitro selection of zinc fingers with altered DNA-binding specific, Biochemistry 1994, 33:5689–5695; International patent applications WO 96/20951, WO 94/18317, WO 96/06166 and WO95119431; and U.S. Ser. No. 60/084819.

Additional Domains and Linkers

Additional domains may be included in the fusion proteins of this invention.

For example, the fusion proteins may contain a nuclear localization sequence (NLS) which provides for the protein to be translocated to the nucleus. A NLS can be located at the N-terminus or the C-terminus of a fusion protein, or can be located between component portions of the fusion protein, so long as the function of fusion protein and its components is disrupted by presence of the NLS. Typically a nuclear localization sequence has a plurality of basic amino acids, referred to as a bipartite basic repeat (reviewed in Garcia-Bustos et al. (1991) Biochimica et Biophysica Acta 1071:83–101). One illustrative NLS is derived from the NLS of the SV40 large T antigen which is comprised of amino acids proline-lysine-lysine-lysine-arginine-lysine-valine (SEQ ID NO:22) (Kalderon et al. (1984) Cell 39:499–509). Another illustrative NLS is derived from a p53 protein. Wild-type p53 contains three C-terminal nuclear localization signals, comprising residues 316–325, 369–375 and 379–384 of p53 (Shaulsky et al. (1990) Mol. Cell. Biol. 10:6565–6577). Other NLSs are described by Shaulsky et al (1990) supra and Shaulsky et al. (1991) Oncogene 6:2056.

To facilitate their detection and/or purification, the fusion proteins may contain peptide portions such as "histidine tags", a glutathione-S-transferase domain or an "epitope tag" which can be recognized by an antibody.

The intervening distance and relative orientation of the various component domains of the fusion proteins can be varied to optimize their production or performance. The design of the fusion proteins may include one or more "linkers", comprising peptide sequence (which may be naturally/occurring or not) separating individual component polypeptide sequences. Many examples of linker sequences, their occurrence in nature, their design and their use in fusion proteins are known. See e.g. Huston et al. (1988) PNAS 85:4879; U.S. Pat. No. 5,091,513; and Richardson et al. (1988) Science 240:1648–1652.

Target Gene Constructs

A target gene construct comprises a gene of interest operably linked to an expression control sequence which permits ligand-regulated expression of the gene. More specifically, such a construct typically comprises: (1) one or more copies of a DNA sequence recognized by a DNA binding domain of a fusion protein of the invention (or by a DNA binding protein like RXR which binds to a fusion protein of the invention); (2) a promoter sequence consisting minimally of a TATA box and initiator sequence but optionally including other transcription factor binding sites; (3) sequence encoding the desired product, including sequences that promote the initiation and termination of translation, if appropriate; (4) an optional sequence consisting of a splice donor, splice acceptor, and intervening intron DNA; and (5) a sequence directing cleavage and polyadenylation of the resulting RNA transcript. Typically the construct contains a copy of the target gene to be expressed, operably linked to an expression control sequence comprising a minimal promoter and one or more copies of a DNA recognition sequence responsive to the transcription factor.

(a) Target Genes

A wide variety of genes can be employed as the target gene, including genes that encode a therapeutic protein, antisense sequence or ribozyme of interest, or any other protein which is of therapeutic or scientific interest. The target gene (and there may be multiple target genes) can encode a gene product which provides a desired phenotype. It can encode a membrane-bound or membrane-spanning protein, a secreted protein, or a cytoplasmic protein. The proteins which are expressed, singly or in combination, can involve homing, cytotoxicity, proliferation, differentiation, immune response, inflammatory response, clotting, thrombolysis, hormonal regulation, angiogenesis, etc. The polypeptide encoded by the target gene may be of naturally occurring or non-naturally occurrring peptide sequence.

Various secreted products include hormones, such as insulin, human growth hormone, glucagon, pituitary releasing factor, ACTH, melanotropin, relaxin, lepfin,etc.; growth factors, such as EGF, IGF-1, TGF-alpha, beta, PDGF, GCSF, MCSF, GM-CSF, FGF, erythropoietin, thrombopoietin, megakaryocytic growth factors, nerve growth factors, etc.; proteins which stimulate or inhibit angiogenesis such as angiostatin, endostatin and VEGF and variants thereof; interleukins, such as IL-1 to -15; TNF-alpha and -beta; and enzymes and other factors, such as tissue plasminogen activator, members of the complement cascade, performs, superoxide cismutase; coagulation-related factors such as antithrombin-III, Factor V, Factor VII, Factor VIIIc, vWF, Factor IX, alpha-anti-trypsin, protein C, and protein S; endorphins, dynorphin, bone morphogenetic protein, CFTR, etc.

The gene can encode a naturally-occurring surface membrane protein or a protein made so by introduction of an appropriate signal peptide and transmembrane sequence. Various such proteins include homing receptors, e.g. L-selectin (Mel-14), hematopoietic cell markers, e.g. CD3, CD4, CD8, B cell receptor, TCR subunits alpha, beta, gamma or delta, CD10, CD19, CD28, CD33, CD38, CD41, etc., receptors, such as the interleukin receptors IL-2R, IL4R, etc.; receptors for other ligands including the various hormones, growth factors, etc.; receptor antagonists for such receptors and soluble forms of such receptors; channel proteins, for influx or efflux of ions, e.g. H+, $Ca^{+2}$, K+, Na+, Cl-, etc., and the like; CFTR, tyrosine activation motif, zap-70, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a veside. This process in conjunction with the presence of the chimeric proteins for exocytosis allows for rapid transfer of the proteins to the extracellular medium and a relatively high localized concentration.

The target gene product can be an intracellular protein such as a protein involved in a metabolic pathway, or a regulatory protein, steroid receptor, transcription factor, etc., By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly keratinocyte stem cells, one could provide for protection against infection, by secreting alpha, beta or gamma interferon, antichemotactic factors, proteases specific for bacterial cell wall proteins, various anti-viral proteins,etc.

In various situations, one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. Regulated expression of a membrane protein which recognizes or binds to the particular site of interest, for example, provides a method for directing the engineered cells to that site. Thus one can achieve a localized concentration of a secreted product or effect cell-based healing, scavenging, protection from infection, anti-tumor activity, etc. Proteins of interest include homing receptors, e.g. L-selectin, GMP140, CLAM-1, etc., or addressins, e.g. ELAM-1, PNAd, LNAd, etc., clot binding proteins, or cell surface proteins that respond to localized gradients of chemotactic factors.

In one embodiment, recognition elements for a DNA binding domain of one of the subject fusion proteins are introduced into the host cells such that they are operatively linked to an endogenous target gene, e.g. by homologous recombination with genomic DNA. A variety of suitable approaches s are available. See, e.g., PCT publications WO93/09222, WO95/31560, WO96/29411, WO95/31560 and WO94/12650. This permits ligand-mediated regulation of the transcription of the endogenous gene.

(b) Minimal Promoters.

Minimal promoters which may be incorporated into a target gene construct (or other construct of the invention) may be selected from a wide variety of known sequences, including promoter regions from fos, hCMV, SV40 and IL-2, among many others. Illustrative examples are provided which use a minimal CMV promoter or a minimal IL2 gene promoter (−72 to +45 with respect to the start site; Siebenlist et al., MCB 6:3042–3049, 1986)

(c) DNA Recognition Sequences.

The choice of recognition sequences to use in the target gene construct is in some cases determined by the nature of the regulatory system to be employed.

Where the target gene construct comprises an endogenous gene with its own regulatory DNA, the recognition sequence is thereby provided by the cells. and the practitioner provides a DNA binding domain which recognizes it.

In systems relying on a tetR or RXR-type DNA binding domain, the recognition sequence is again usually predetermined (by the choice of tetR or RXR-type DNA binding domain).

In other cases, e.g., in ligand-mediated crosslinking systems and systems like the progesterone receptor-based system, a diverse set of DNA binding domain:recognition sequence choices are available to the practitioner.

Recognition sequences for a wide variety of DNA-binding domains are known. DNA recognition sequences for other DNA binding domains may be determined experimentally. In the case of a composite DNA binding domain, DNA recognition sequences can be determined experimentally, or the proteins can be manipulated to direct their specificity toward a desired sequence. A desirable nucleic acid recognition sequence for a composite DNA binding domain consists of a nucleotide sequence spanning at least ten, preferably eleven, more preferably twelve or more, and even more preferably in some cases eighteen bases. The component binding portions (putative or demonstrated) within the nucleotide sequence need not be fully contiguous; they may be interspersed with "spacer" base pairs that need not be directly contacted by the chimeric protein but rather impose proper spacing between the nucleic acid subsites recognized by each module. These sequences should not impart expression to linked genes when introduced into cells in the absence of the engineered DNA-binding protein.

To identify a nucleotide sequence that is recognized by a chimeric protein containing a DNA-binding region, preferably recognized with high affinity (dissociation constant $10^{-11}$ M or lower are especially preferred), several methods can be used. It high-affinity binding sites for individual subdomains of a composite DNA-binding region are already known, then these sequences can be joined with various spacing and orientation and the optimum configuration determined experimentally (see below for methods for determining affinities). Alternatively, high-affinity binding sites for the. protein or protein complex can be selected from a large pool of random DNA sequences by adaptation of published methods (Pollock, R. and Treisman, R., 1990, A sensitive method for the determination of protein-DNA binding specificities. *Nucl. Acids Res.* 18, 6197–6204). Bound sequences are cloned into a plasmid and their precise sequence and affinity for the proteins are determined. From this collection of sequences, individual sequences with desirable characteristics (i.e., maximal affinity for composite protein, minimal affinity for individual subdomains) are selected for use. Alternatively, the collection of sequences is used to derive a consensus sequence that carries the favored base pairs at each position. Such a consensus sequence is synthesized and tested to confirm that it has an appropriate level of affinity and specificity.

The target gene constructs may contain multiple copies of a DNA recognition sequence. For instance, the constructs may contain 5, 8, 10 or 12 recognition sequences for GAL4 or for ZFHD1.

Design and Assembly of the DNA Constructs

Constructs may be designed in accordance with the principles, illustrative examples and materials and methods disclosed in the patent documents and scientific literature cited herein, with modifications and further exemplification as described. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector for transducing host cells and permitting the expression of the protein. For biochemical analysis of the encoded chimera, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

Introduction of Constructs Into Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human and mouse cells are of particular interest. Across the various species, various types of cells may be used, such as hematopoietic, neural, glial, mesenchymal, cutaneous, mucosal, stromal, muscle (including smooth muscle cells), spleen, reticuloendothelial, epithelial, endothelial, hepatic, kidney, gastrointestinal, pulmonary, fibroblast, and other cell types. Of particular interest are muscle cells (including skeletal, cardiac and other muscle cells), cells of the central and peripheral nervous systems, and hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells The cells may be autologous cells, syngeneic cells, allogeneic cells and even in some cases, xenogeneic cells with respect to an intended host organism. The cells may be modified by changing the major histocompatibility complex ("MHC") profile, by inactivating β2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, and the like.

In some instances specific clones or oligoclonal cells may be of interest, where the cells have a particular specificity, such as T cells and B cells having a specific antigen specificity or homing target site specificity.

Constructs encoding the fusion proteins and comprising target genes of this invention can be introduced into the cells as one or more nucleic acid molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional domain may be isolated, where one or more mutations may be introduced using "primer repair", ligation, in vitro mutagenesis, etc. as appropriate.

The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Alternatively, the construct may be introduced by protoplast fusion, electroporation, biolistics, calcium phosphate transfection, lipofection, microinjection of DNA or the like.

The host cells will in some cases be grown and expanded in culture before introduction of the construct(s), followed by the appropriate treatment for introduction of the construct(s) and integration of the construct(s). The cells will then be expanded and screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, Cell (1987) 51, 503–512; Mansour, et al., Nature (1988) 336, 348–352; and Joyner, et at., Nature (1989) 338,153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, and mammalian expression control elements, etc. which may be used to prepare stocks of construct DNAs and for carrying out transfections are well known in the art, and many are commercially available.

Introduction of Constructs Into Animals

Any means for the introduction of genetically engineered cells or heterologous DNA into animals, preferably mammals, human or non-human, may be adapted to the practice of this invention for the delivery of the various DNA constructs into the intended recipient. For the purpose of this discussion, the various DNA constructs described herein may together be referred to as the transgene.

By Ex Vivo Genetic Engineering

Cells which have been transduced ex vivo or in vitro with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). After being transduced with the heterologous genetic constructs, the modified host cells may be identified, selected, gorwon, characterized, etc. as desired, and then may be used as planned, e.g. grown in culture or introduced into a host organism.

Depending upon the nature of the cells, the cells may be introduced into a host organism, e.g. a mammal, in a wide variety of ways, generally by injection or implantation into the desired tissue or compartment, or a tissue or compartment permitting migration of the cells to their intended destination. Illustrative sites for injection or implantation include the vascular system, bone marrow, muscle, liver, cranium or spinal cord, peritoneum, and skin. Hematopoietic cells, for example, may be administered by injection into the vascular system, there being usually at least about $10^4$ cells and generally not more than about $10^{10}$ cells. The number of cells which are employed will depend upon the circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213–24 (HepG2 cells/hydroxyethyl methacrylate-methyl methacrylate membranes); Chang et al, 1993, Hum Gene Ther 4(4):433–40 (mouse Ltk-cells expressing hGH/ immunoprotective perm-selective alginate microcapsules; Reddy et al, 1993, J Infect Dis 168(4):1082–3 (alginate); Tai and Sun, 1993, FASEB J 7(11): 1061–9 (mouse fibroblasts expressing hGH/alginate-poly-L-lysine-alginate membrane); Ao et al, 1995, Transplantation Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an imnnunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91 (23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more fusion proteins containing component domains derived from proteins of the host species and/or from viral proteins or proteins from species other than the host species. The cells may be derived from one or more individuals other than the recipient and may be derived from a species other than that of the recipient organism or patient.

By In Vivo Genetic Engineering

Instead of ex vivo modification of the cells, in many situations one may wish to modify cells in vivo. A variety of techniques have been developed for genetic engineering of target tissue and cells in vivo, including viral and non-viral systems.

In one approach, the DNA constructs are delivered to cells by transfection, i.e., by delivery to cells of "naked DNA", lipid-complexed or liposome-formulated DNA, or otherwise formulated DNA. Prior to formulation of DNA, e.g., with lipid, or as in other approaches, prior to incorporation in a final expression vector, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal. See, e.g., Canonico et al, Am J Respir Cell Mol Biol 10:24–29, 1994 (in vivo transfer of an aerosolized recombinant human alpha1-antitrypsin gene complexed to cationic liposomes to the lungs of rabbits); Tsan et al, Am J Physiol 268 (Lung Cell Mol Physiol 12): L1052–L1056, 1995 (transfer of genes to rat lungs via tracheal insufflation of plasmid DNA alone or complexed with cationic liposomes); Alton et al., Nat Genet. 5:135–142, 1993 (gene transfer to mouse airways by nebulized delivery of cDNA-liposome complexes). In either case, delivery of vectors or naked or formulated DNA can be carried out by instillation via bronchosoopy, after transfer of viral particles to Ringer's, phosphate buffered saline, or other similar vehicle, or by nebulization.

Viral systems include those based on viruses such as adenovirus, adeno-associated virus, hybrid adeno-AAV, lentivirus and retroviruses, which allow for transduction by infection, and in some cases, integration of the virus or transgene into the host genome. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The virus may be administered by injection (e.g. intravascularly or intramuscularly), inhalation, or other parenteral mode. Non-viral delivery methods such as administration of the DNA via complexes with liposomes or by injection, catheter or biolistics may also be used. See e.g. WO 96/41865, PCT/US97/22454 and U.S. Ser. No. 60/084819, for example, for additional guidance on formulation and delivery of recombinant nucleic acids to cells and to organisms.

By employing an attenuated or modified retrovirus carrying a target transcriptional initiation region, if desired, one can activate the virus using one of the subject transcription factor constructs, so that the virus may be produced and transduce adjacent cells.

The use of recombinant viruses to deliver the nucleic acid constructs are of particular interest. The transgene(s) may be incorporated into any of a variety of viruses useful in gene therapy.

In clinical settings, the gene delivery systems (i.e., the recombinant nucleic acids in vectors, virus, lipid formulation or other form) can be introduced into a patient, e.g., by any of a number of known methods. For instance, a pharmaceutical preparation of the gene delivery system can be introduced systemically, e.g. by intravenous injection, inhalation, etc. In some systems, the means of delivery provides for specific or selective transduction of the construct into desired target cells. This can be achieved by regional or local administration (see U.S. Pat. No. 5,328, 470) or by stereotactic injection, e.g. Chen et al., (1994) PNAS USA 91: 3054–3057 or by determinants of the delivery means. For instance, some viral systems have a tissue or cell-type specificity for infection. In some systems cell-type or tissue-type expression is achieved by the use of cell-type or tissue-specific expression control elements controlling expression of the gene.

Those references as well as the references cited previously, including those relating to tetR-based systems, progesterone-receptor-based systems and ecdysone-based systems, provide detailed additional guidance on the preparation, formulation and delivery of various ligands to cells in vitro and to organisms.

In preferred embodiments of the invention, the subject expression constructs are derived by incorporation of the genetic construct(s) of interest into viral delivery systems including a recombinant retrovirus, adenovirus, adeno-associated virus (AAV), hybrid adenovirus/AAV, herpes virus or lentivirus (although other applications may be carried out using recombinant bacterial or eukaryotic plasmids). While various viral vectors may be used in the practice of this invention, AAV- and adenovirus-based approaches are of particular interest for the transfer of exogenous genes in vivo, particularly into humans and other mammals. The following additional guidance on the choice and use of viral vectors may be helpful to the practitioner, especially with respect to applications involving whole animals (including both human gene therapy and the development and use of animal model systems), whether ex vivo or in vivo.

Viral Vectors:

Adenoviral Vectors

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genone rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide targetell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription domains that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan (1990) Radiotherap. Oncol. 19:197). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584). Adenovirus vectors have also been used in vaccine development (Grunhaus and Horwitz (1992) Seminar in Virology 3:237; Graham and Prevec (1992). Biotechnology 20:363). Experiments in administering recombinant adenovirus to different tissues include trachea instillation (Rosenfeld et al. (1991); Rosenfeld et al. (1992) Cell 68:143), muscle injection (Ragot et al. (1993) Nature 361:647), peripheral intravenous injection (Herz and Gerard (1993) Proc. Natl. Acad. Sci. U.S.A. 90:2812), and stereotactic inoculation into the brain (Le Gal La Salle et al. (1993) Science 254:988).

Furthermore, the virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109–127). Expression of the inserted gene can be under control of, for example, the E1A promoter, the major late promoter (MLP) and associated leader sequences, the viral E3 promoter, or exogenously added promoter sequences.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector. As stated above, the typical vector according to the present invention is replication defective and will not have an adenovirus E1 region. Thus, it will be most convenient to introduce the nucleic acid of interest at the position from which the E1 coding sequences have been removed. However, the position of insertion of the nucleic acid of interest in a region within the adenovirus sequences is not critical to the present invention. For example, the nucleic add of interest may also be inserted in lieu of the deleted E3 region in E3 replacement vectors as described previously by Karsson et. al. (1986) or in the E4 region where a helper cell line or helper virus complements the E4 defect.

A preferred helper cell line is 293 (ATCC Accession No. CRL1573). This helper cell line, also termed a "packaging cell line" was developed by Frank Graham (Graham et al. (1987) J. Gen. Virol. 36:59–72 and Graham (1977) J.General Virology 68:937–940) and provides E1A and E1B in trans. However, helper cell lines may also be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

Various adenovirus vectors have been shown to be of use in the transfer of genes to mammals, including humans. Replication-deficient adenovirus vectors have been used to express marker proteins and CFTR in the pulmonary epithelium. Because of their ability to efficiently infect dividing cells, their tropism for the lung, and the relative ease of generation of high titer stocks, adenoviral vectors have been the subject of much research in the last few years, and various vectors have been used to deliver genes to the lungs of human subjects (Zabner et al., Cell 75:207–216, 1993; Crystal, et al., Nat Genet. 8:42–51, 1994; Boucher, et al., Hum Gene Ther 5:615–639, 1994). The first generation E1a deleted adenovirus vectors have been improved upon with a second generation that includes a temperature-sensitive E2a viral protein, designed to express less viral protein and thereby make the virally infected cell less of a target for the immune system (Goldman et al., Human Gene Therapy 6:839–851,1995). More recently, a viral vector deleted of all viral open reading frames has been reported (Fisher et al., Virology 217:11–22, 1996). Moreover, it has been shown that expression of viral IL-10 inhibits the immune response to adenoviral antigen (Qin et al., Human Gene Therapy 8:1365–1374, 1997).

Adenoviruses can also be cell type specific, i.e., infect only restricted types of cells and/or express a transgene only in restricted types of cells. For example, the viruses comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by the same methods (restriction digest, linker ligation or filling in of ends, and ligation) used to insert the CFTR or other genes into the vectors.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.;PCT/FR94/00851 (WO 95/02697) by Perrocaudet et al., PCT/US95/14793 (WO96/14061) by Wang et al.

AAV Vectors

Another viral vector system useful for delivery of DNA is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells or muscle cells, and exhibits a high frequency of stable integration (see for example Flotte et al., (1992) Am. J. Respir. Cell. Mol. Biol. 7:349–356; Samulski et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

The AAV-based expression vector to be used typically indudes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the recombinant DNA encoding the fusion protein(s), e.g. fusion proteins comprising an activation domain or DNA-binding domain, an AAV promoter can be used (ITR itself or AAV p5 (Flotte, et al. J. Biol.Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap (which are obligatory for replication and packaging of the recombinant viral construct) under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Typically, three days after transfection, recombinant AAV is harvested from the cells along with adenovirus and the contaminating adenovirus is then inactivated by heat treatment.

Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Alternatively, a cell can be transformed with a first AAV vector including a 5' ITR, a 3' ITR flanking a heterologous gene, and a second AAV vector which includes an inducible origin of replication, e.g., SV40 origin of replication, which is capable of being induced by an agent, such as the SV40 T antigen and which includes DNA sequences encoding the AAV rep and cap proteins. Upon induction by an agent, the second AAV vector may replicate to a high copy number, and thereby increased numbers of infectious AAV particles may be generated (see, e.g, U.S. Pat. No. 5,693,531 by Chiorini et al., issued Dec. 2, 1997. In yet another method for producing large amounts of recombinant AAV, a plasmid is used which incorporate the Epstein Barr Nuclear Antigen (EBNA) gene, the latent origin of replication of Epstein Barr virus (oriP) and an AAV genome. These plasmids are maintained as a multicopy extra-chromosomal elements in cells, such as in 293 cells. Upon addition of wild-type helper functions, these cells will produce high amounts of recombinant AAV (U.S. Pat. No. 5,691,176 by Lebkowski et al., issued Nov. 25, 1997). In another system, an AAV packaging plasmid is provided that allows expression of the rep gene, wherein the p5 promoter, which normally controls rep expression, is replaced with a heterologous promoter (U.S. Pat. No. 5,658,776, by Flotte et al., issued Aug. 19, 1997). Additionally, one may increase the efficiency of AAV transduction by treating the cells with an agent that facilitates the conversion of the single stranded form to the double stranded form, as described in Wilson et al., WO96/39530.

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J.Biol. Chem.

268:3781–3790, 1993) or chromatographic purification, as described in O'Riordan et al., WO97/08298.

Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (Jan. 10, 1989); Muzyczka et al, U.S. Pat. No. 5,139,941 (Aug. 18, 1992); Lebkowski et al, U.S. Pat. No. 5,173,414 (Dec. 22, 1992); Srivastava, U.S. Pat. No. 5,252,479 (Oct. 12, 1993); Lebkowski et al, U.S. Pat. No. 5,354,678 (Oct. 11, 1994); Shenk et al, U.S. Pat. No. 5,436,146(Jul. 25, 1995); Chatterjee et al, U.S. Pat. No. 5,454,935 (Dec. 12, 1995), Carter et al WO 93/24641 (published Dec. 9, 1993), and Natsoulis, U.S. Pat. No. 5,622,856 (Apr. 22, 1997). Further information regarding AAVs and the adenovirus or herpes helper functions required can be found in the following articles. Berns and Bohensky (1987), "Adeno-Associated Viruses: An Update", Advanced in Virus Research, Academic Press, 33:243–306. The genome of AAV is described in Laughlin et al. (1983) "Cloning of infectious adeno-associated virus genomes in bacterial plasmids", Gene, 23: 65–73. Expression of AAV is described in Beaton et al. (1989) "Expression from the Adeno-associated virus p5 and p19 promoters is negatively regulated in trans by the rep protein", J. Virol., 63:4450–4454. Construction of rAAV is described in a number of publications: Tratschin et al. (1984) "Adeno-associated virus vector for high frequency integration, expression and rescue of genes in mammalian cells", Mol. Cell. Biol., 4:2072–2081; Hermonat and Muzyczka (1984) "Use of adeno-associated virus as a mammalian DNA cloning vector: Transduction of neomycin resistance into mammalian tissue culture cells", Proc. Natl. Acad. Sci. USA, 81:6466–6470; McLaughlin et al. (1988) "Adeno-associated virus general transduction vectors: Analysis of Proviral Structures", J. Virol., 62:1963–1973; and Samulski et al. (1989) "Helper-free stocks of recombinant adeno-associated viruses: normal integration does quote viral gene expression", J. Virol., 63:3822–3828. Cell lines that can be transformed by rAAV are those described in Lebkowski et al. (1988) "Adeno-associated virus: a vector system for efficient introduction and integration of DNA into a variety of mammalian cell types", Mol. Cell. Biol., 8:3988–3996. "Producer" or "packaging" cell lines used in manufacturing recombinant retroviruses are described in Dougherty et al. (1989) J. Virol., 63:3209–3212; and Markowitz et al. (1988) J. Virol., 62:1120–1124.

Hybrid Adenovirus-AAV Vectors

Hybrid Adenovirus-AAV vectors represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in the this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0–1) and includes the 5' ITR and the packaging/enhancer domain. The 3' adenovirus sequences of the hybrid virus include the right terminal 3' ITR sequence which is about 580 nucleotides (about bp 35,353- end of the adenovirus, referred to as about map units 98.4–100.

The AAV sequences useful in the hybrid vector are viral sequences from which the rep and cap polypeptide encoding sequences are deleted and are usually the cis acting 5' and 3' ITR sequences. Thus, the AAV ITR sequences are flanked by the selected adenovirus sequences and the AAV ITR sequences themselves flank a selected transgene. The preparation of the hybrid vector is further described in detail in published PCT application entitled "Hybrid Adenovirus-AAV Virus and Method of Use Thereof", WO 96/13598 by Wilson et al.

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

Retroviruses

The retroviruses are a group of single-stranded RNA viruses characterized by an ability to convert their RNA to double-stranded DNA in infected cells by a process of reverse-transcription (Coffin (1990) Retroviridae and their Replication" In Fields, Knipe ed. Virology: New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsidal proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer: New York: Plenum Press; Mann et al., 1983, supra). The media containing the recombinant retroviruses is then collected, optionally concentrated, and used for gene transfer. Retroviral vectors are able to infect a broad variety of cell types. However, integration and stable expression require the division of host cells (Paskind et al. (1975) Virology 67:242).

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(Xbal) (Sawyers et al. (1995) J. Exp. Med. 181:307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem.266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Other Viral Systems

Other viral vector systems that may have application in gene therapy have been derived from herpes virus, e.g., Herpes Simplex Virus (U.S. Pat. No. 5,631,236 by Woo et al., issued May 20, 1997), vaccinia virus (Ridgeway (1988) Ridgeway, "Mammalian expression vectors," In: Rodriguez R L, Denhardt D T. ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1–10), and several RNA viruses. Preferred viruses include an alphavirus, a poxvirus, an arena virus, a vaccinia virus, a polio virus, and the like. In particular, herpes virus vectors may provide a unique strategy for persistence of the recombinant gene in cells of the central nervous system and ocular tissue (Pepose et al., (1994) Invest Ophthalmol Vis Sci 35:2662–2666). They offer several attractive features for various mammalian cells (Friedmann (1989) Science, 244:1275–1281; Ridgeway, 1988, supra; Baichwal and Sugden, 1986, supra; Coupar et al., 1988; Horwich et al.(1990) J.Virol., 64:642–650).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, supra). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al. (1991) Hepatology, 14:124A).

Administration of Viral Vectors

Generally the DNA or viral particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles. Delivery of the transgene as naked DNA; as lipid-, liposome-, or otherwise formulated DNA; or as a recombinant viral vector is then preferably carried out via in vivo, lung-directed, gene therapy. This can be accomplished by various means, including nebulization/inhalation or by instillation via bronchoscopy. Recently, recombinant adenovirus encoding CFTR was administered via aerosol to human subjects in a phase I clinical trial. Vector DNA and CFTR expression were clearly detected in the nose and airway of these patients with no acute toxic effects (Bellonet al., Human Gene Therapy, 8(1):15–25, 1997).

Preferably, the DNA or recombinant virus is administered insufficient amounts to transfect cells within the recipient's airways, including without limitation various airway epithelial cells, leukocytes residing within the airways and accessible airway smooth muscle cells, and provide sufficient levels of transgene expression to provide for observable ligand-responsive transcription of a target gene, preferably at a level providing therapeutic benefit without undue adverse effects.

Optimal dosages of DNA or virus depends on a variety of factors, as discussed previously, and may thus vary somewhat from patient to patient. Again, therapeutically effective doses of viruses are considered to be in the range of about 20 to about 50 ml of saline solution containing concentrations of from about $1\times10^7$ to about $1\times10^{10}$ pfu of virus/ml, e.g. from $1\times10^8$ to $1\times10^9$ pfu of virus/ml.

In a preferred embodiment, the ratio of viral particle containing containing a target gene versus viral particles containing nucleic acids encoding the fusion proteins of the invention is about 1:1. However, other ratios can also be used. For example, in certain instances it may be desirable to administer twice as many particles having the target gene as those encoding the fusion proteins. Other ratios include 1:3, 1:4, 1:10, 2:1, 3:1, 4:1, 5:1, 10:1. The optimal ratio can be determined by performing in vitro assays using the different ratios of viral particles to determine which ratio results in highest expression and lowest background expression of the target gene. Similarly, in situations in which the fusion proteins are encoded by two different nucleic acids each encapsidated separately, one can vary the ratio between the three viral particles, according to the result desired.

Methods of the Invention

The invention provides methods for engineering cells to render them responsive to ligand-mediated regulation of expression of a target gene. The cells may be engineered in vitro (ex vivo) or in vivo (i.e., in situ—within an organism). The target gene can be an endogenous gene or an exogenous gene (which may be of naturally occurring peptide sequence, or may contain non-naturally occurring peptide sequence). The method comprises introducing into the cell(s) of interest one or more genetic constructs or compositions of this invention. Examples of these methods include the genetic engineering of cells or animals (e.g., mice, rats, etc.) as described herein for use, e.g., in the study of normal or pathological biological processes (including various diseases), for the identification or characterization of genes or for the identification of new drugs or the evaluation of drug functioning, mechanism or efficacy. Other examples include the delivery of gene therapy to human subjects, whether in vivo or ex vivo.

The invention also provides methods for using such engineered cells, or organisms containing them, to carry out the objectives mentioned above and elsewhere herein as well as in the cited references. These methods generally involve the application of ligand to the engineered cells or organism containing them in order to regulate the expression of a target gene.

Kits

This invention further provides kits useful for the various applications. One such kit contains one or more nucleic acids, each encoding a fusion protein of the invention. The kit may further comprise an additional nucleic acid comprising a target gene construct. Alternatively, the additional nucleic acid may contain a cloning site for insertion of a desired target gene by the practitioner. The kit may further contain a sample of a ligand for regulating gene expression using these materials.

Uses

In one application, cells engineered in accordance with the invention are used to produce a target protein in vitro. In such applications, the cells are cultured or otherwise maintained until production of the target protein is desired. At that time, the appropriate ligand is added to the culture medium, in an amount sufficient to cause the desired level of target protein production. The protein so produced may be recovered from the medium or from the cells, and may be purified from other components of the cells or medium as desired.

Proteins for commercial and investigational purposes are often produced using mammalian cell lines engineered to express the protein. The use of mammalian cells, rather than bacteria, insect or yeast cells, is indicated where the proper function of the protein requires post-translational modifications not generally performed by non-mammalian cells. Examples of proteins produced commercially this way include, among others, erythropoietin, BMP-2, tissue plasminogen activator, Factor VIII:c, Factor IX, and antibodies. The cost of producing proteins in this fashion is related to the level of expression achieved in the engineered cells. Thus, because the invention described herein can achieve considerably higher expression levels than conventional expression systems, it may reduce the cost of protein production. Toxicity of target protein production can represent a second limitation, preventing cells from growing to high density and/or reducing production levels. Therefore, the ability to tightly control protein expression, as described herein, permits cells to be grown to high density in the absence of protein production. Expression of the target gene can be activated and the protein product subsequently harvested, only after an optimum cell density is reached, or when otherwise desired.

In other applications, cells within an animal host or human subject are engineered in accordance with the invention, or cells so engineered are introduced into the animal or human subject, in either case, to prepare the recipient for ligand-mediated regulation of expression of a target gene. In the case of non-human animals, this can be done as part of veterinary treatment of the animal or to create an animal model for a variety of research purposes. In the case of human subjects, this can be done as part of a therapeutic or prophylactic treatment program.

This invention is applicable to a variety of treatment approaches. For example, the target gene to be regulated can be an endogenous gene or a heterologous gene, and its expression may be activated or repressed by addition of ligand.

In some cases the target gene is a factor necessary for the proliferation and/or differentiation of one or more cell types of interest. For example, it may be desirable to stimulate the expression of growth factors and lymphokines in a subject in which at least some of the blood cells have been destroyed, e.g., by radiotherapy or chemotherapy. For example, expression of erythropoietin stimulates the production of red blood cells, expression of G-CSF stimulates the production of granulocytes, expressionof GM-CSF stimulates the prodution of various white blood cells, etc. Similarly in diseases or conditions in which one or more specific cell types are destroyed by the disease process, e.g., in autoimmune diseases, the specific cells can be replenished by stimulating expression of one or more genes encoding factors stimulating proliferation of these cells. The method of the invention can also be used to increase the number of lymphocytes in a subject having AIDS, such as by stimulating expression of lymphokines, e.g., IL-4, which stimulates proliferation of certain T helper (Th) cells.

At least one advantage of increasing the production of an endogenous protein in a subject is the absence of an immune reaction against the protein, thus resulting in a more efficient treatment of the subject. In some cases of regulated expression of a heterologous protein, it may be preferable to simultaneously administer to the subject an immunosuppressant drug, e.g., rapamycin, cyclosporin A, FK506 or a mixture of any of the foregoing or other compound which represses immune reactions.

Cells which have been modified ex vivo with the DNA constructs of the invention may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

In cases in which the target gene is an endogenous gene of the cells to be engineered, the promoter and/or one or more other regions of the gene can be modified to include a target sequence that is specifically recognized by the DNA binding domain of a fusion protein of this invention so that the endogenous target gene is specifically recognized and regulated in a ligand-dependent manner. Such an embodiment can be useful in situations in which no DNA binding protein is known to specifically bind to a regulatory region of the target gene. Thus, in one embodiment, one or more cells are obtained from a subject or other source and genetically engineered in vitro such that a desired control element is inserted, operatively linked to the target gene. The cell can then be introduced into the subject. Alternatively, prior to introduction of the cell to the subject, the cell is further modified to include a nucleic acid encoding a fusion protein comprising a DNA binding domain which is capable of interacting specifically with the expression control element introduced into the target gene. In other examples of the invention, an endogenous gene is modified in vivo by, e.g., homologous recombination, a technique well known in the art, and described, e.g., in Thomas and Capecchi (1987) Cell 51:503; Mansour et al. (1988) Nature 336:348; and Joyner et al. (1989) Nature 338:153.

A target gene may encode antisense RNA or a ribozyme or other RNA molecule which is not translated. For example, the method of the invention can be used to inhibit production of one or more specific proteins in a cell of a subject. The availability of potent transcriptional activators provided by the invention will ensure that high levels of RNA, e.g., antisense RNA, are produced in a cell.

Other uses for this invention include biological research. The two-hybrid assay is a transcription based assay first described by Fields and Song, Nature, 340:245–247 (1989). See also, Fields et al, U.S. Pat. No. 5,283,173 (Feb. 1, 1994). The two-hybrid assay is based on the observation that transcription factors contain separable functional modules that direct either DNA binding or transcription activation. A DNA binding domain expressed in cells will bind to DNA but not activate transcription as it lacks a transcription activation domain. Conversely, a transcription activation domain alone will not effect transcription in the absence of directed and/or intimate interaction with DNA such as would be provided by a DNA-binding domain. However, if the DNA binding domain and the transcription activation domains are each expressed as part of separate fusion proteins, and the fusion protects are capable of associating, the "two-hybrid" complex so formed represents a reconstituted transcription factor (see FIG. 1). Such a reconstituted transcription factor is capable of initiating transcription of a reporter gene (e.g., a gene for a conveniently detectable marker such as beta-galactosidase or alkaline phosphatase (SEAP) or a protein important for cell viability) located downstream of DNA binding sites recognized by the DNA-binding domain. The amount of reporter gene expression, i.e., the amount of gene product produced, will reflect the extent to which the fusion proteins complex with one another. As described in Example 8, use of the bundling domains of this invention to recruit additional activation domains to the complex significantly increases the sensitivity of the assay, such that interactions which were previously undetected are now clearly visible.

This dramatic improvement has important ramifications for a variety of applications of the 2-hybrid methodology, including those aimed at identifying genes of interest, at identifying peptide binding partners, and at identifying inhibitors of a protein-protein interaction of interest.

For instance, to identify genes of interest, e.g. cDNAs from a cDNA library, the genes are cloned into a construct designed to express the encoded polypeptides as fusion proteins linked to a bundling domain and to a transcription activation domain. As an example of the design of such constructs, one may start with a construct encoding a fusion protein such as an RLS fusion protein depicted in FIG. 3, but replace the DNA sequence encoding a ligand binding domain with a cloning site for the insertion of the cDNAs. The constructs (bearing the cDNA inserts) are introduced into host cells containing (or subsequently made to contain) (i) a nucleic acid encoding a fusion protein containing a DNA binding domain and a target domain of interest, and (ii) a reporter gene construct containing a recognition sequence for the DNA binding domain operably linked to a gene which encodes a detectable gene product or which is otherwise responsible for a detectable phenotype. Cells expressing a fusion protein containing a cDNA-encoded domain which binds to the target domain of interest express the reporter gene construct. The corresponding cDNA can thus be identified based on the fact that the protein it encodes binds to the target domain of interest. Potential advantages include the enhanced ability to detect and identify less abundant cDNAs, cDNAs which are expressed at lower levels relative to other cDNAs, cDNAs encoding gene products which bind to the target with relatively lower affinity, etc.

In another 2-hybrid application, a collection of polypeptides may be expressed as fusion proteins using nucleic acid constructs encoding the desired collection of polypeptides in place of the cDNAs in the previous example. Peptide sequences which bind to a target protein or domain of interest may thus be identified.

Another such application involves assays for identifying inhibitors of protein:protein interactions of interest. In such assays a host cell is engineered to express two fusion proteins, the first containing a DNA binding domain and a first protein domain of interest, the second fusion protein containing a transcription activation domain, a bundling domain and a second protein domain of interest which binds to the first protein domain of interest. The cells also contain a reporter gene construct as described above. Because the two fusion proteins bind to one another, the reporter gene is normally expressed. Such cells may be used to identify compounds which inhibit the protein:protein interaction, for instance in a drug screening program. Thus, cells containing fusion proteins of this invention may be contacted with one or more compounds to be tested. The presence or amount of reporter gene product is then measured. A decrease in reporter gene expression in the presence of a substance, as compared to expression in the presence of less or none of the substance, indicates that the substance inhibited the protein::protein interaction. For additional details on the design and implementation of such assays which can be adapted to this invention, see e.g. WO 95/24419. Substances for testing may be obtained from a wide variety of sources, including without limitation, microbial broths, cellular extracts, conditioned media from cells, combinatorial libraries and other sources of naturally occurring or synthetic compounds.

Pharmaceutical Compositions & Their Administration to Subjects Containing Engineered Cells Administration The ligand may be administered to a human or non-human subject using pharmaceutically acceptable materials and methods of administration. Various formulations, routes of administration, dose and dosing schedule may be used for the administration of ligand, depending upon factors such as the binding affinity of the ligand for the ligand binding domain, the choice of transcription regulatory domains, the condition and cirmcumstances of the recipient, the response desired, the biological half-life and bioavailability of the ligand, the biological half-life and specific activity of the target gene product, the number and location of engineered cells present, etc. The drug may be administered parenterally, or more preferably orally. Dosage and frequency of administration will depend upon factors such as described above. The drug may be taken orally as a pill, powder, or dispersion; bucally; sublingually; injected intravascularly, intraperitoneally, subcutaneously; or the like. The drug (and antagonists, as discussed below) may be formulated using conventional methods and materials well known in the art for the various routes of administration. The precise dose and particular method of administration will depend upon the above factors and be determined by the attending physician or healthcare provider. However, we show here that in the presence of bundled activation domains, the amount of drug needed to oligomerize the fusion proteins of this system is greatly reduced, by an order of magnitude or more.

The particular dosage of the drug for any application may be determined in accordance with conventional approaches and procedures for therapeutic dosage monitoring. A dose of the drug within a predetermined range is given and the patient's response is monitored so that the level of therapeutic response and the relationship of target gene expression level over time may be determined. Depending on the expression levels observed during the time period and the therapeutic response, one may adjust the level of subsequent dosing to alter the resultant expression level over time or to otherwise improve the therapeutic response. This process may be iteratively repeated until the dosage is optimized for therapeutic response. Where the drug is to be administered chronically, once a maintenance dosage of the drug has been determined, one may conduct periodic follow-up monitoring to assure that the overall therapeutic response continues to be achieved.

In the event that the activation by the drug is to be reversed, administration of drug may be suspended so that cells return to a basal rate of proliferation. To effect a more active reversal of therapy, an antagonist of the drug may be administered. An antagonist is a compound which binds to the drug or drug-binding domain to inhibit interaction of the drug with the fusion protein(s) and thus inhibit the downstream biological event. Antagonists include drug analogs, homologs or components which are monovalent with respect to the fusion proteins. Such compounds bind to the fusion proteins but do not support clustering of the fusion proteins as is required for activation of signaling. Thus, in the case of an adverse reaction or the desire to terminate the therapeutic effect, an antagonist can be administered in any convenient way, particularly intravascularly or by inhalation/nebulization, if a rapid reversal is desired.

Compositions

Drugs (i.e., the ligands) for use in this invention can exist in free form or, where appropriate, in salt form. The preparation of a wide variety of pharmaceutically acceptable salts is well-known to those of skill in the art. Pharmaceutically acceptable salts of various compounds include the conventional non-toxic salts or the quaternary ammonium salts of such compounds which are formed, for example, from inorganic or organic acids of bases.

The drugs may form hydrates or solvates. It is known to those of skill in the art that charged compounds form hydrated species when lyophilized with water, or form solvated species when concentrated in a solution with an appropriate organic solvent.

The drugs can also be administered as pharmaceutical compositions comprising a therapeutically (or prophylactically) effective amount of the drug, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositons for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intrapetitoneal or subcutaneous injection. Sterile solutions can also be administered intravenously. The drugs can also be administered orally either in liquid or solid composition form.

The carrier or excipient may include time delay material well known to the art, such as glyceryl monostearate or glyceryl distearate along or with a wax, ethylcellulose, hydroxypropylmcthylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) may be used as an oral formulation for a variety of drugs for use in the practice of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the drug may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the drugs, or the various formulations thereof, including tablets, capsules, injectable solutions, encapsulation in liposomes, microparticles, microcapsules, etc. Preferred routes of administration to a patient are oral, sublingual and bucal. Methods of introduction also could include but are not limited to dermal, intradermal, intramuscular, intraperitoneal, intravenous, subcutaneous, intranasal, pulmonary, epidural, ocular and (as is usually preferred) oral routes. The drug may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For ex vivo applications, the drug will be delivered as a liquid solution to the cellular composition.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral administration).

The effective dose of the drug will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. In embodiments in which the compound is rapamycin or an analog thereof with some residual immunosuppressive effects, it is preferred that the dose administered be below that associated with undue immunosuppressive effects.

The amount of a given drug which will be effective in the treatment or prevention of a particular disorder or condition will depend in part on the severity of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The drugs can also be provided in a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceutical or biological products, which notice reflects approval by the agency of manufacture, use or sale for human administration.

The full contents of all references cited in this document, including references from the scientific literature, issued patents and published patent applications, are hereby expressly incorporated by reference.

The following examples contain important additional information, exemplification and guidance which can be adapted to the practice of this invention in its various embodiments and the equivalents thereof. The examples are offered by way illustration should not be construed as limiting in any way. As noted throughout this document, the invention is broadly applicable and permits a wide range of design choices by the practitioner.

The practice of this invention will employ, unless otherwise indicated, conventional techniques of cell biology, cell culture, molecular biology, transgenic biology, microbiology, recombinant DNA, immunology, virology, pharmacology, chemistry, and pharmaceutical formulation and administration which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Bibliography

Allen, J. B., Walberg, M. W., Edwards, M. C. & Elledge, S. J. (1995) Finding prospective partners in the library: the two hybrid system and phage display fins a match. Trends Bio Sci, 511–516.

Ballard, D. W., Dixon, E. P., Peffer, N. J., Bogerd, H., Doerre, S., Stein, B. & Greene, W. C. The 65 kDa subunit of human NF-kB functions as a potent transcriptional activator and a target for v-Rel-mediated repression, Proc. Natl. Acad. Sci. USA, 89, 1875–1879.

Baron, U; Gossen, M & Bujard, H. (1997) Tetracycline-controlled transcription in eukaryotes: novel transactivators with graded transactivation potential. Nuc. Acid. res, 25, 2723–2729.

Belshaw, P. J., Ho, S. N., Crabtree, G. R. & Schreiber, S. L. (1996) Controlling protein association and subcellular localization with a synthetic ligand that induces heterodimerization of proteins. Proc. Natl. Acad. Sci. 93, 4604–4607.

Blair, W. S., Bogerd, H. P., Madore, S. J. & Culilen, B. R. (1994) Mutational analysis of the transciption activation domain of ReIA: Identification of a highly synergistic minimal acidic activation module. Mol. Cell. Biol. 14, 7226–7234.

Brent, R. & Ptashne, M. (1985) Cell 43, 729–736.

Cress, W. D. & Triezenberg, S. J. (1990) Critical structural elements of the VP16 activation domain. Science 251, 87–90.

Emami, K. H. & Carey, M. (1992) A synergistic increase of a multimerized VP16 transcriptional activation domain. EMBO J. 11, 5005–5012.

Fields, S. & Song, O-K. (1989) Nature 340, 245–246.

Fields, S. & Sternglanz, R. (1994) The two-hybrid system: an assay for protein-protein interactions. Trends Genet 10, 286–292.

Friedman, A. M., Fischmann, T. O. & Steiz, T. A. (1995) Crystal structure of Iac repressor core tetramer and its implications for DNA looping. Science 268, 1721–1727.

Gerber, H-P., Seipel, K., Georgiev, O., Hofferer, M., Hug, M., Rusconi, S. & Schaffner, W. Transcriptional activation modulated by homopolymeric glutamine and proline stretches. Science 263, 808–811.

Hope, I. A. & Struhl, K. (1 986) Cell 46. 885–894.

Iwabuch, K., Li., B., Bartel, P. & Fields, S. (1993) Use of the two-hybrid system to identify the domain of p53 involved in oligomerization. Oncogene 8, 1693–1696.

Keegan, L., Gill, G. & Ptashne, M. (1986) Science 231, 699–704.

McKnight, J., Kristie, T. & Roizman, B. (1987) Proc. Natl. Acad. Sci. 88, 9578–9582.

Moore, P. A., Ruben, S. M., & Rosen, C. A. (1993) Conservation of transcriptional activation functions of the NF-kB p50 and p65 subunits in mammalian cells and Saccharomyces cerevisiae. Mol. Cell. Biol. 13, 1666–1674.

Natesan, S., Rivera, V. M., Molinari, E and Gilman, M. (1997) Transcriptional squelching re-examined. Nature 390, 349–350

Ohashi, Y., Brickman, J. M., Furman, E., Middleton, B. & Carey, M. (1994) Modulating the potency of an activator in a yeasy in vitro transcription system. Mol. Cell. Biol. 14, 2731–2739.

Orphanides, G., Lagrange, T. & Reinberg, D. (1996) The general transcription factors of RNA polymerase II. Genes and Dev. 10, 2657–2683

Pascal, E & Tjian, R. (1991). Different activation domains of SP1 govern formation of multimers and mediate transcriptional synergism. Genes and Dev. 5, 1646–1656.

Ptashne, M. & Gann, A. (1997) Transcriptional activation by recruitment. Nature 386, 569–577.

Rivera, V. M., Clackson, T., Natesan, S., Pollock, R., Amara, J. F., Keenan, T., Magari, S. R., Phillips, T., Courage, N. L., Cerasoli, F Jr., Holt, D. A. & Gilman, M. (1996) A humanized system for pharmacologic control of gene expression. Nature Med 2, 1028–1032.

Sauer, F., Hansen, S. K & Tjian, R. (1995) Multiple TAFIIs directing synergistic activation of transcription. Science 270, 1783–1788.

Sadowski, I., Ma, J., Triezenberg, S. & Ptashne, M. (1988) GAL4-VP16 is an unusually potent transcriptional activator. Nature 335, 563–564. Schmitz, M. L. & Baeuerle, P. A. (1991) The p65 subunit is responsible for the strong transcription activating potential of NF-kB. EMBO J. 12, 3805–3817.

Schmitz, M. L., dos Santos Silva, M. A., Altmann, H., Czsich, M., Holak, T. A. & Baeuerle, P. A. (1994) Structural and functional analysis of the NF-KB p65 C terminus. An acidic and modular transactivation domain with the potential to adopt an alpha-helical conformation. J. Biol. Chem. 269, 25613–25620.

SenGuptha, D. J., Zhang, B., Kraemer, B., Pochart, P., Fields, S. & Wickens, M. (1996) A three-hybrid system to detect RNA-protein interactions in vivo. Proc. Natl. Acad. Sci. USA 93, 8496–8501.

Tanaka, M. (1996) Modulation of promoter occupancy by cooperative DNA binding and activation-domain function is a major determinant of transcriptional regulation by activators in vivo. Proc Natl Acad Sci USA 93, 4311–4315.

Tanaka, M., Clouston, W. M. & Herr. W. (1994) The Oct-2 glutamine-rich and proline-rich activation domains can synergize with each other or duplicates of themselves to activate transcription. Mol. Cell. Biol. 14, 6046–6055.

Tjian, R., & Maniatis, T. (1994). Transcriptional activation: a complex puzzle with few easy pieces. Cell 77, 5–8.

Triezenberg, S. J. (1995) Structure and function of transcription activation domains. Curr. Biol. 5, 190–196.

Uesugi, M., Nyanguile, O., Lu, H., Levine, A. J. & Verdine, G. L. (1997) Induced a helix in the VP16 activation domain upon binding to a human TAF. Science 277, 1310–1313.

EXAMPLES

Example 1

Construction of Plasmids Encoding Bundled Activation Domains

Transcription factor fusion proteins were expressed from pCGNN (Attar, R. M. & Gilman, M. Z. (1992) Expression cloning of a novel zinc-finger protein that binds to the c-fos serum response element. *Mol. Cell. Biol.* 12, 2432–2443). Inserts cloned into pCGNN as XbaI-BamHI fragments are transcribed under control of the human CMV enhancer and promoter and are expressed with an amino-terminal epitope tag (a 16-amino acid portion of the Haemophilus influenzae hemagglutinin gene) and nuclear localization sequence from the SV40 large T antigen. Individual components of the transcription factors were synthesized by polymerase chain reaction as fragments containing an XbaI site immediately upstream of the first codon and a SpeI site, an in-frame stop codon, and a BamHI site immediately downstream of the last codon. Fusion proteins comprising multiple component were assembled by stepwise insertion of XbaI-BamHI fragments into SpeIBamHI-opened vectors. The individual components used and their abbreviations are as follows:

G=yeast Gal4 DNA binding domain, amino adds 1–94

F=human FKBP12, amino acids 1–107

R=FRB domain of human FRAP, amino acids 2025–2113

S=activation domain from the p65 subunit of human NF-kB, amino acids 361–550

V=activation domain from Herpesvirus VP16, amino acids 410–494

L=*E. coli* lactose repressor, amino acids 46–360

MT=Minimal Tetramerization domain of *E. coli* lactose repressor, amino acids 324–360

For example, pCGNN-GF2 was made by insertion of the Gal4 DNA binding domain into pCGNN to generate pCGNN, followed by the sequential insertion of 2 FKBP domains. POGNN-L was made inserting the Xba1/BamH1 digested PCR fragments of lactose repressor coding sequences (amino acids 46–360) into PCGNN vector. PCGNN-LS was made by inserting p65 activation domain (amino acids 361–550) into Spe1 and BamH1 digested PCGNN-L expression plasmid. PCGNN-GAL4 CB was made by inserting Xba1 and BamH1 digested fragments of c-CBL sequences into Spe1 and BamH1 digested PCGNN-GAL4 expression plasmid. PCGNN-MA was made by inserting Xba1 and BamH1 digested DNA fragments containing SH3 domain coding sequences into Xba1/BamH1 digested PCGNN. PCGNN-MAS and PCGNN-MAMTS were made by inserting the S (p65 activation domain) and MTS (minimal tetramerization domain fused to p65 activation domain) respectively into Spe1/BamH1 digested PCGNN-MA vector. 5×GAL4-IL2-SEAP contains 5 GAL4 sites upstream of a minimal IL2 promoter driving expression of the SEAP gene (a gift of J. Morgenstern and S. Ho). The retroviral vector pLH-5×Gal4-IL2-SEAP was constructed by cloning the 5×GAL4-IL2-SEAP fragment described above into the vector pLH (Rivera et al, 1996, Nature Medicine 2:1028–1032; Natesan et al, Nature 1997 Nov 27 390:6658 349–50), which also contains the hygromycin B resistance gene driven by the Moloney murine leukemia virus long terminal repeat.

Example 2

Generation of Stable Cell Lines

To generate cells containing the pLH-5×GAL4-IL2-SEAP reporter stably integrated, helper-free retrovirus, generated as described (Rivera et al, 1996; Natesan et al, 1997), was used to infect HT1080 cells. Hundreds of hygromycin B (300 mg/ml) resistant clones were pooled (HT1080 B pool) and individual clones screened by transient transfection with pCG-GS. The most responsive clone, HT1080B, was selected for further analysis.

Example 3

Transient Transfections

HT1080 cells were grown at 37° C. in MEM medium containing 10% fetal calf serum, non-essential amino acids and penicillin-streptomycin. Twenty-four hours before transfection, approximately $2\times10^5$ cells were seeded in each well in a 12-well plate. Cells were transfected using Lipofectamine as recommended (Gibco BRL). Cells in each well received the amounts plasmids indicated in the figure, with or without 400 ng of reporter plasmid, with the total amount of DNA being adjusted to 1.25 ug with pUC19. For experiments shown in FIG. 5, 10 ng of plasmid expressing DNA binding domain fusions and increasing amounts of plasmid expressing p65 activation domain fusions were included. After transfection for five hrs, the medium was removed and 1 ml of fresh medium added. 18–24 hrs later, 100 ul medium was removed and assayed for SEAP activity using a Luminescence Spectrometer (Perkin Elmer) at 350 nm excitation and 450 nm emission. Where indicated, 2–5 ul of medium was also assayed for hGH protein as recommended (Nichols Diagnostic).

Example 4

Delivery of Bundled Activation Domains to the GAL4 DNA Binding Domain

Figure 1A:
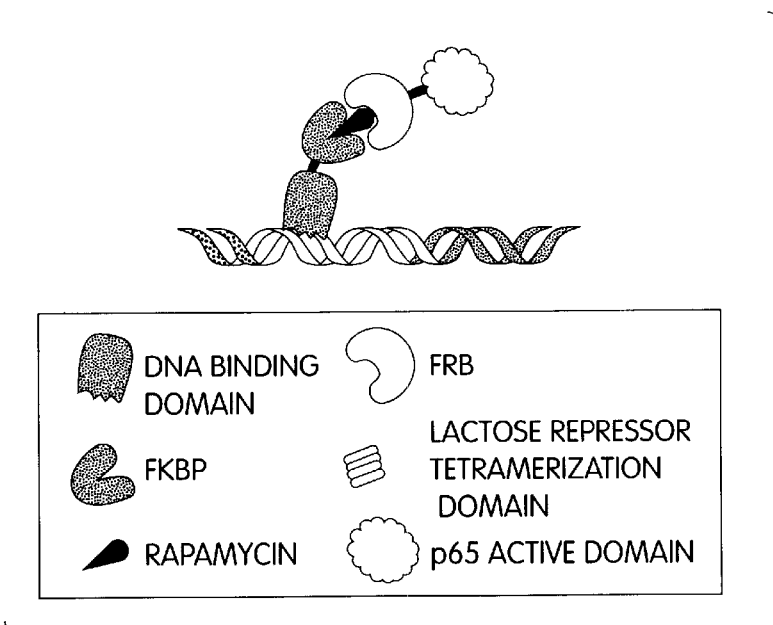
Figure 1B:
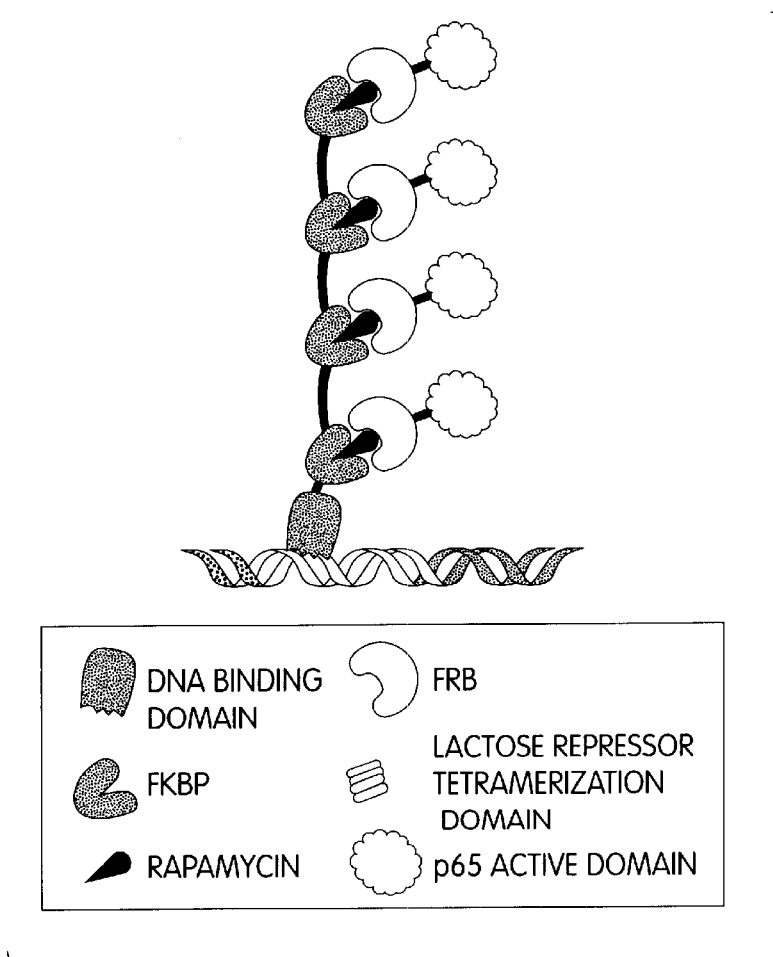
Figure 1C:
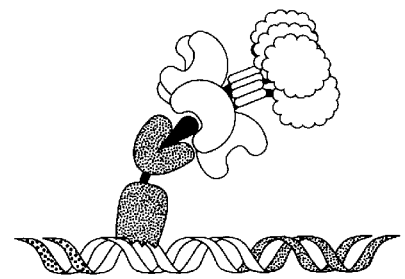
Figure 1C:
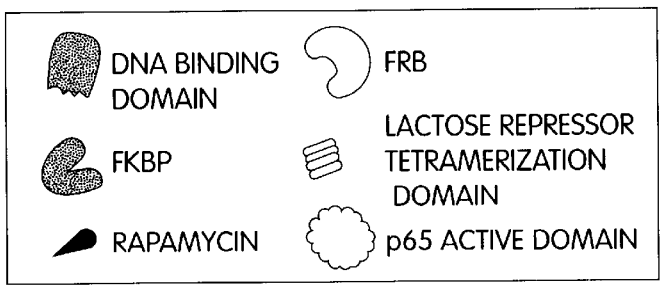
Figure 1D:
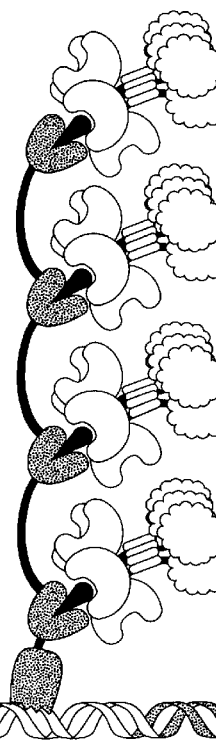
Figure 1D:
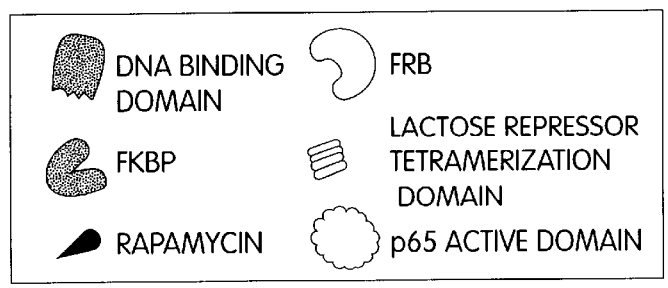
Figure 1E:
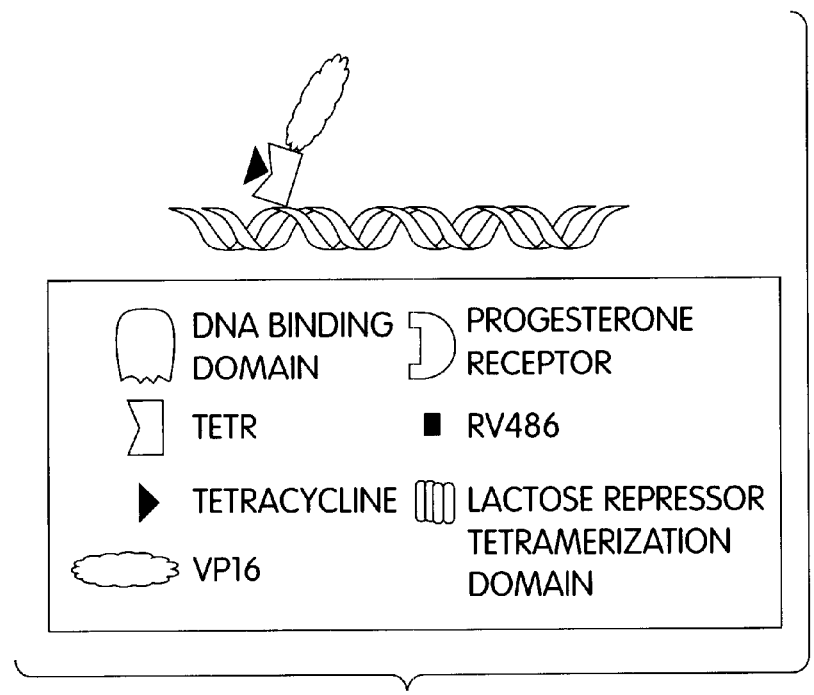
Figure 1F:
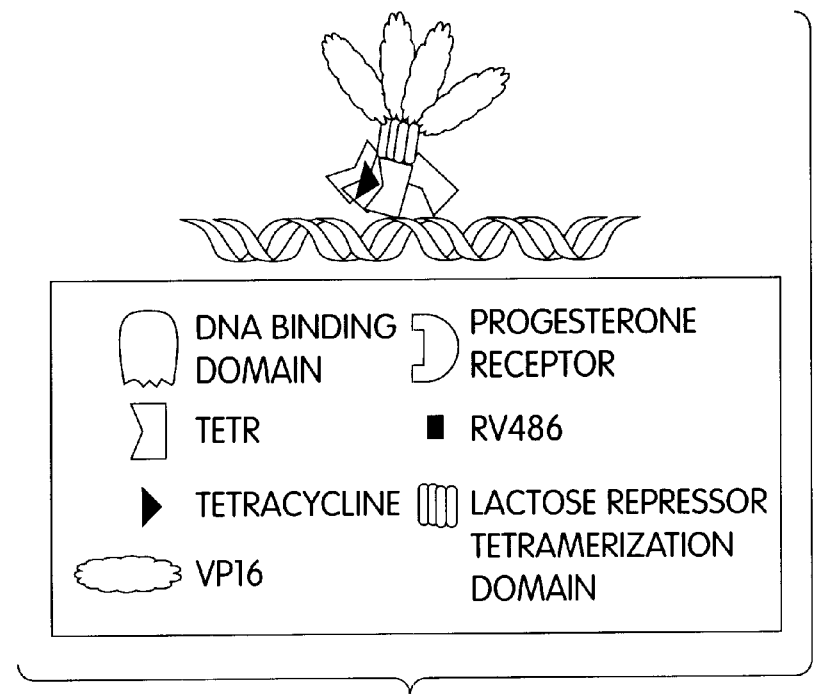
Figure 1G:
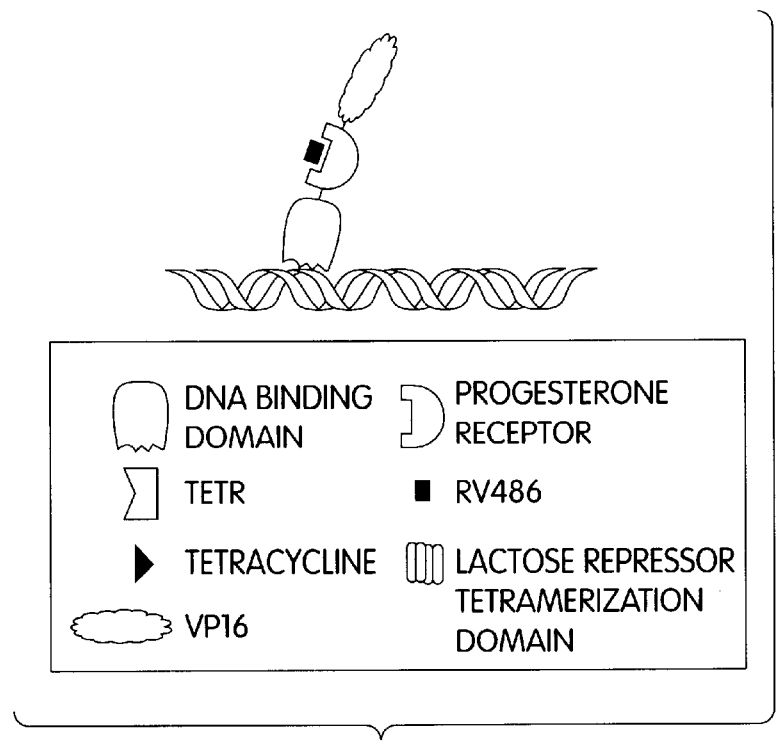
Figure 1H:
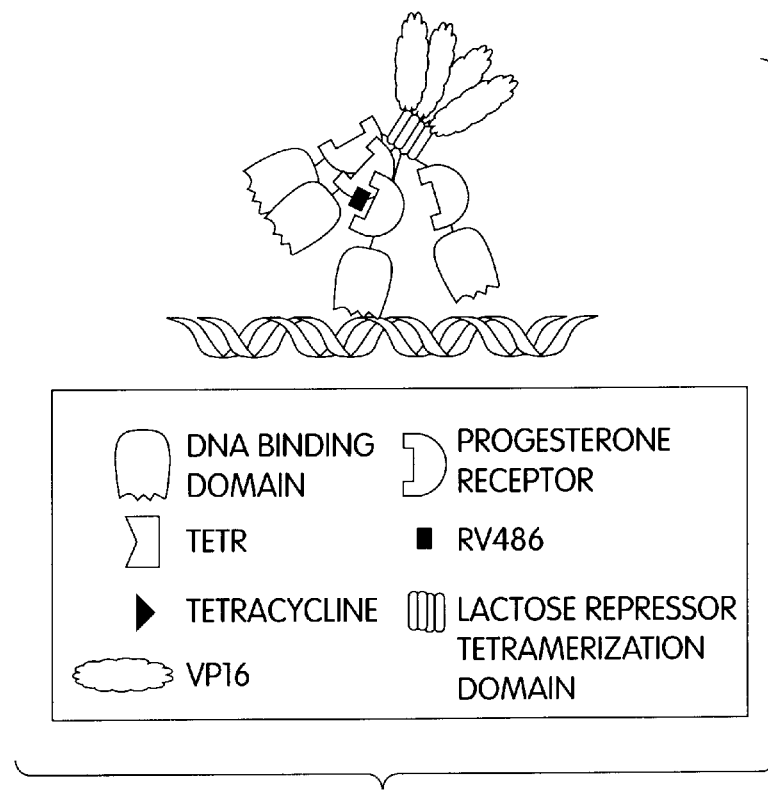

The basic system used for regulated gene expression (FIG. 1A)involves two fusion proteins, one containing a DNA-binding domain (such as GAL4) fused to a single copy of FKBP12 and the other containing a transcription activation domain (such as from the p65 subunit of NF-kB) fused to the FRB domain of FRAP (see e.g., Rivera et al). In the presence of the natural-product rapamycin, which forms a high affinity complex with FKBP and FRB domains, the FRB-p65 fusion protein is efficiently recruited to the GAL4-FKBP fusion protein. This basic system results in the delivery of a maximum of one p65 activation domain per DNA binding domain monomer (FIG. 1A). In this system the number of activation domains delivered to the promoter can be increased by fusing multiple FKBP moieties to GAL4, allowing each DNA binding domain to recruit multiple FRB-p65 activation domain fusions (FIG. 1B). Because the fusion protein containing the activation domain is expressed separately in this system, it is possible to bundle activation domain fusion proteins and deliver them to FKBP moieties linked to the GAL4 DNA binding domain. For example, the addition of a tetramerization domain present in the E. coli lactose repressor between the FRB and activation domains should generate a fusion protein "bundle" comprising of four activation domains and FRB domains, which in the presence of "dimerizer" can be delivered to each FKBP moiety (FIG. 1C). In the configuration depicted in FIG. 1D rapamycin mediates the recruitment of a tetrameric complex of bundled activation domain fusion proteins to each FKBP of a Gal4-4×FKBP fusion protein, permitting recruitment of up to sixteen p65 activation domains to a single GAL4 monomer. Analogous improvements on allostery-based systems, also based on bundling, are shown in FIGS. 1E–1H.

Example 5

Transcriptional Activation is Proportional to the Number of Activation Domains Bound to the Promoter To test how bundled activation domain fusion proteins function in this system, we transfected HT1080 B cells with plasmids expressing various transcription factor fusion proteins and treated the cells with 10 nM rapamycin to deliver the activation domains to the promoter. We observed that when only one RS or RLS fusion protein is delivered to each GAL4 monomer (GF1+RS and GF1+RLS), bundled activation domain fusion proteins induced the reporter gene strongly as compared to the unbundled activation domain fusion proteins. This finding suggests that bundled activation domain fusion proteins, because of their ability to deliver more activation domains to the promoter, function as highly potent inducers of transcription. Furthermore, our studies using various combinations of DNA binding fusion proteins and activation domain fusion proteins revealed that the level of reporter gene expression is roughly linear with the number of activation domains that can be delivered to a single GAL4 monomer bound to its promoter (FIG. 2A).

The RLS fusion protein is capable of delivering four times more p65 activation domain to the promoter than its unbundled counterpart, RS. In theory, FRB fusion protein containing four tandemly reiterated p65 activation domain (RS4) should deliver same number of activation domains to the promoter as RLS and therefore should have similar transactivation capacity. To examine whether RS4 can function in a manner similar to RLS in the rapamycin regulated gene expression system, we transfected expression plasmids encoding the DNA binding receptor, GF1, together with RS4 or RLS fusion proteins into HT1080 B cells and analyzed the expression of the integrated reporter gene by adding 10 nM rapamycin to the medium. We found that rapamycin induced the reporter gene strongly in cells expressing the GF1 and RLS but not the GF1 and RS4 combination of fusion proteins, indicating that the reiterated p65 activation domains are weak inducers of transcription in the dimerizer system (FIG. 2B). In contrast, rapamycin was able to induce reporter gene expression in the presence of the GF3 and RS4 combination of fusion proteins, albiet at much lower levels than the GF1/RLS combination of proteins. Without being limited to a particular theory, GF3 fusion proteins should recruit three times more activation domains to the promoter than GF1. The finding that RS4 fusion protein can induce transcriptional activation much more strongly when tethered to GF3 as compared to GF1, suggests that when the concentration of activation domain fusion protein is very low, more activation domains can be recruited to the promoter by increasing the number of FKBP moieties fused to the GAL4 DNA binding domain. A western blot analysis of the intracellular levels of the transfected proteins revealed that the amount of RS4 in the cell is below the level of detection, which may explain why it acts as a poor induce of transcription. These observations strongly suggest that the bundling strategy, unlike reiteration, generates highly potent activation domains that are less toxic to cells.

One possible explanation for part or all of the robust induction of gene expression by RLS fusion proteins is that the close proximity of four FRB moieties in the RLS bundle produces an avidity effect. To test this, we devised a strategy as illustrated in FIG. 3A. In theory, co-expressing a limited amount of RLS in the presence of a large excess of LS fusion protein should promote the formation of RLS bundles containing, at most, a single FRB domain. To examine the consequences of reducing the number of FRB domains in the RLS bundle on reporter gene expression, we co-transfected HT1080 B cells with relevant expression plasmids and analyzed the expression of the GAL4 responsive gene in the presence of 10 nM rapamycin in the medium. As previously observed (see FIG. 2A), rapamycin induced only low levels of reporter gene expression in cells expressing GF1 and RS fusion proteins. However, reporter gene expression was very robust in cells expressing GF1 and RLS fusion proteins (FIG. 3B). To our surprise, in cells expressing GF1, a limited amount of RLS and a large excess of LS fusion protein, rapamycin induced reporter gene expression to even higher levels than those achieved by GF1 and RLS fusion proteins alone (FIG. 3B). This suggests that the strong stimulation of gene expression by RLS fusion proteins is not dependent on the presence of multiple FRB domains in the bundle. Indeed, the data shown here indicates that the presence of multiple FRB domains in RLS fusion protein actually diminishes its capacity to activate gene expression to the maximum possible level. It is likely that rapamycin allows multiple FRB domains in the RLS to make contact with more than one GAL4-FKBP monomer bound to the promoter, effectively reducing the number of activation domains delivered. However, RLS bundles with a single FRB domain can make contact with only a single GAL4-FKBP monomer and therefore can recruit greater number of activation domains to the promoter, leading to a slight increase in the target gene expression.

To assess the consequences of reducing the number of activation domains in the RLS fusion protein, we expressed excess amounts of lactose repressor region (L, amino acids 46–340) relative to RLS, together with the DNA binding protein GF1 and induced reporter gene expression by adding 10 nM rapamycin to the medium. In this situation, the tetrameric bundles formed should contain a maximum of one activation domain and one FRB domain. cause reducing the number of FRB domains in the RLS bundle increased reporter gene expression, any inhibition of reporter gene expression in the presence of excess L region relative to RLS can be attributed to a decline in the number of activation domains recruited to the promoter. The data in FIG. 3B show that an excess of a portion of the lactose repressor inhibits rapamycin-induced reporter gene expression in cells expressing GF1 and RLS fusion proteins. A western blot analysis of the recombinant proteins in the transfected cells shows a good correlation between the amount of plasmid used in the transfection and the corresponding expression level of protein. Taken together, these observations strongly suggest that the RLS fusion proteins function as potent inducers of transcription primarily because of their ability to deliver significantly more activation domains to the promoter.

Example 6

Activation of Transcription Using a Minimal Tetramerization Domain and Synergizing Activation Domains The experiments described used the lactose repressor (minus its DNA binding domain) as the bundling domain in fusino proteins also containing the FRB and activation domains. In addition to the tetramerization domain, this portion of lactose repressor contains the lactose binding domain and the flanking linker regions. To determine whether the tetramerization domain of lactose repressor alone is sufficient for bundling fusion proteins, we made an expression plasmid, RMTS, in which the lactose repressor coding sequences (amino acids 46–360) in the RLS fusion protein was replaced with a thirty-six amino acid region between amino acids 324 and 360 containing the tetramerization domain and a portion of upstream linker region (MT, We have found that combination of p65 and VP16 activation domains when fused to GAL4 DNA binding domain synergistically induced GAL responsive genes. To examine whether they behave similarly when bundled together using the minimal lactose repressor minimal tetramerization domain, we generated two additional plasmids, RMTSV and RMTV in which the VP16 activation domain (amino acids 419–490) was fused to RMTS or RMT respectively. We then co-transfected plasmids expressing appropriate combinations of fusion proteins (FIG. 4) into HT1080 B cells carrying a stably integrated GAL4 responsive reporter gene and treated the cells with rapamycin to stimulate target gene expression. We observed that in cells expressing GF4/RMTSV and GF4/RMTS combination of fusion proteins, rapamycin induced the reporter gene expression to roughly six and three fold higher than GF4/RS combination of fusion proteins. In cells expressing GF4/RMTV or GF4/RSV combinations of fusion proteins, rapamycin induced the reporter gene only marginally higher than the levels induced by GF4/RS fusion proteins (FIG. 4). Although the fold induction of reporter gene expression by GF4/RMTS and GF4/RMTSV is slightly lower than GF4/RLS and GF4/RLSV, three and six fold compared to four and eight fold respectively (see FIG. 2A), strong stimulation of gene expression by the activation domain fusion proteins containing the lactose repressor minimal tetramerization domain suggest that the minimal tetramerization domain is sufficient to bundle fusion proteins.

Example 7

Bundling Reduces the Threshold Number of Activators Required to Induce Peak Levels of Gene Expression If the strong stimulation of gene expression induced by the bundled fusion proteins containing p65 activation domains is simply due to their ability to deliver more activation domains to the promoter, a lower level of fusion protein containing the activation domain should be sufficient in the case of bundling, as compared to unbundled activation domains, to strongly stimulate reporter gene expression. In the dimerizer system, the number of reconstituted activators formed can be controlled either by adjusting the amount of activation domain fusion proteins or by varying the amount of rapamycin added to the medium. We have employed both of these complementary approaches to address the question of whether bundling of activation domains reduces the threshold amount of activators required for robust expression of the reporter gene. In the first approach, varying amounts of bundled activation domains, RMTS and RMTSV, or their unbundled counterpart, RS, were expressed in HT1080 B cells together with a fixed amount of GF4, the DNA binding receptor (FIG. 5A) The activators were reconstituted by the addition of 10 nM rapamycin to the medium. The level of recombinant proteins expressed in the transfected cells was determined by western blot analysis (FIG. 5B). At the lowest level of activation domains expressed, rapamycin failed to induce transcription of the reporter gene in cells expressing the GF4+RS combination of fusion proteins. However, we observed robust activation of reporter gene expression in cells containing the GF4+RMTS or RMTSV combination of fusion proteins. When the activation domain fusion proteins were present at high levels, rapamycin induced reporter gene expression to approximately four-and two-fold higher levels in cells containing the GF4+RMTSV and GF4+RMTS combination of fusion proteins, respectively, as compared to GF4+RS fusion proteins. Indeed, the level of reporter gene expression induced by the lowest amounts of RMTSV exceeded the level stimulated by the highest amount of RS fusion proteins in the cell. (FIG. 5A). These observations suggest that peak levels of reporter gene expression can be achieved with fewer reconstituted activators containing bundled activation domains than with their unbundled counterparts.

In the second complementary approach, we transfected HT1080 B cells with a fixed amount of the expression plasmids used in FIG. 5B and induced the reconstitution of the activators by adding varying amounts of rapamycin to the medium. In the presence of the GF4 DNA binding receptor, both RMTSV and RMTS fusion proteins induced the reporter gene expression robustly at 1 nM rapamycin in the medium. At this concentration of rapamycin in the medium, the GF4+RS combination of fusion proteins failed to induce the reporter gene significantly above background levels. In all cases, we observed peak levels of reporter gene expression in the presence of 10 nM rapamycin in the medium (FIG. 5B). Collectively, the finding that relatively low numbers of activators containing multiple bundled activation domains are sufficient to strongly induce gene expression suggests that the threshold amount of activators required for peak levels of gene expression can be significantly lowered by increasing the potency of activators.

Example 8

Bundling Activation Domain Fusion Proteins in the Two-hybrid System Enhances its Sensitivity The finding that robust expression of target genes can be achieved in the presence of relatively few reconstituted activators containing bundled, but not unbundled, activation domain fusion proteins has important implications in two-hybrid assays. Although the two-hybrid system is a highly sensitive assay to detect protein-protein interactions in vivo, a number of factors may curtail the interaction between two hybrid proteins expressed in the cell. One frequently faced problem with the two hybrid system is that eukaryotic cells, because of their highly conserved biochemical regulatory pathways, often exhibit poor tolerance to high levels of the hybrid proteins, particularly those containing the potent VP16 activation domain, resulting in the very poor expression of fusion proteins in these cells, or in some cases, cell death. Because the success of this assay is dependent on the two hybrid proteins finding each other, it is essential that one or both of the hybrid proteins, preferably the fusion protein containing the activation domain, is present at relatively high amounts to promote the interaction between the two hybrid proteins.

To examine whether the use of bundled activation domain fusion proteins would allow detection of protein-protein interactions that were previously undetectable in mammalian two-hybrid assays, we chose to study the interaction between two proteins, namely, the proto-oncogene C-Cbl and the C-Src SH3. The proline-rich domains of the C-Cbl proto-oncogene have been shown to bind to the SH3 domains of a number of signaling proteins both in in vitro and in yeast two-hybrid assays. However, in mammalian two-hybrid experiments, the GAL4-CBL and Src SH3-VP16 hybrid proteins failed to induce the expression of a stably integrated reporter gene. To examine whether expressing "bundled" Src SH3-activation domain fusion protein together with GAL4CBL would stimulate the GAL4 responsive gene, we made appropriate plasmids for expressing the fusion proteins shown schematically in FIG. 6A and B, and introduced relevant combinations of expression plasmids into HT1080 B cells by transient transfection. We observed that neither GCBL alone, nor GCBL in the presence SH3-VP16 or SH3-p65, induced the reporter gene expression to detectable levels. However, in the presence of the bundled fusion proteins, SH3-LVP16 or SH3-Lp65, GCBL induced the reporter gene very strongly. These results show that the use of bundled activation domain fusion protein can significantly improve the sensitivity of the two-hybrid assay (FIG. 6C). To assess whether the unbundled activation domain fusion proteins fail to induce the reporter gene expression due to their low intracellular levels, we carried out western blot analysis of lysates from the transfected cells. A representative western blot shown in FIG. 6C illustrates that the unbundled fusion proteins, SH3-VP16 and SH3-p65, were actually present at higher amounts than their bundled counterparts, SH3-LVP16 and SH3-Lp65 (FIG. 6C), suggesting that the lack of reporter gene activation is not linked to the overall intracellular levels of the activation domain fusion proteins. However, in a separate western blot probed with GAL4 antibody, we were unable to detect the presence of Gal4-CBL, suggesting that this fusion protein is toxic to cells. Thus, we conclude that when the DNA binding component (GCBL) is present in very low amounts in the cells, only the bundled activation domain fusion proteins are capable of delivering a sufficient number of activation domains to the promoter for transcriptional activation of the reporter gene to occur. Taken together, these data strongly suggest that bundling activation domain fusion proteins, in mammalian two-hybrid assays, may greatly enhance the detection of interactions between two proteins when one or both of them is present at very low levels in the cell.

Equivalents

Those skilled in the art will recognize, or be able to ascertain using no more than routine experimentation, numerous equivalents to the specific materials and methods described herein. Such equivalents are considered to be within the scope of this invention.

What is claimed is:

1. A recombinant nucleic acid encoding a fusion protein which comprises a tetramerization or tetramerization domain and a composite DNA binding domain.

2. The recombinant nucleic acid of claim 1 wherein said fusion protein comprises a tetramerization domain.

3. The recombinant nucleic acid of claim 1 wherein said fusion protein comprises a tetramerization domain.

4. The recombinant nucleic acid of claim 1 which further comprises a transcription activation domain.

5. The recombinant nucleic acid of claim 1 which further comprises a transcription repression domain.

6. The recombinant nucleic acid of claim 2 which further comprises a transcription activation domain.

7. The recombinant nucleic acid of claim 2 which further comprises a transcription repression domain.

8. The recombinant nucleic acid of claim 3, wherein the tetramerization domain is or is derived from a lac repressor tetramerization domain or a p53 tetramerization domain.

9. The recombinant nucleic acid of claim 3 which further comprises a transcription activation domain.

10. The recombinant nucleic acid of claim 3 which further comprises a transcription repression domain.

11. The recombinant nucleic acid of claim 8 which further comprises a transcription activation domain.

12. The recombinant nucleic acid of claim 8 which further comprises a transcription repression domain.

13. The recombinant nucleic acid of any one of claims 1, 2, 3, 8, 4, 6, 9, 11, 5, 7, 10 or 12 which further contains a ligand binding domain.

14. The recombinant nucleic acid of any one of claims 1, 2, 3, 8, 4, 6, 9, 11, 5, 7, 10 or 12, wherein the composite DNA binding domain comprises a homeodomain.

15. The recombinant nucleic acid of any one of claims 1, 2, 3, 8, 4, 6, 9, 11, 5, 7, 10 or 12, wherein the composite DNA binding domain comprises a zinc finger domain.

16. The recombinant nucleic acid of any one of claims 4, 6, 9 or 11 which comprises a transcription activation domain of 6 to 100 amino acids residues in length.

17. The recombinant nucleic acid of any one of claims 4, 6, 9 or 11 in which the transcription activation domain is or is derived from a VP16 or p65 transcription activation domain.

18. The recombinant nucleic acid any one of claims 5, 7, 10 and 12 in which the transcription repression domain is derived from a Krüppel domain.

19. The recombinant nucleic acid of claim 13 wherein the ligand binding domain is or is derived from an immunophilin, cyclophilin, FRB (FKBP:rapamycin complex binding antibiotic binding domain or hormone receptor domain.

20. The recombinant nucleic acid of claim 16, wherein the composite DNA binding domain comprises a homeodomain.

21. The recombinant nucleic acid of claim 16, wherein the composite DNA binding domain comprises one or more zinc finger domains.

22. The recombinant nucleic acid of claim 17 which comprises part or all of the sequence corresponding to residues 361–550 of a human p65 protein.

23. The recombinant nucleic acid of claim 17, wherein the composite DNA binding domain comprises a homeodomain.

24. The recombinant nucleic acid of claim 17, wherein the composite DNA binding domain comprises one or more zinc finger domains.

25. The recombinant nucleic acid of claim 19 wherein the ligand binding domain is or is derived from FKBP (FK506 binding protein tetR tetracycline repressor progesterone receptor or ecdysone receptor.

26. The recombinant nucleic acid of claim 22, wherein the composite DNA binding domain comprises a homeodomain.

27. The recombinant nucleic acid of claim 22, wherein the composite DNA binding domain comprises one or more zinc finger domains.

28. A vector comprising a recombinant nucleic acid of any one of claims 1, 2, 3, 8, 4, 6, 9, 11, 5, 7, 10 or 12.

29. A vector comprising a recombinant nucleic acid of claim 14.

30. A vector comprising a recombinant nucleic acid of claim 15.

31. A vector comprising a recombinant nucleic acid of claim 20.

32. A vector comprising a recombinant nucleic acid of claim 21.

33. A vector comprising a recombinant nucleic acid of claim 23.

34. A vector comprising a recombinant nucleic acid of claim 24.

35. A vector comprising a recombinant nucleic acid of claim 26.

36. A vector comprising a recombinant nucleic acid of claim 27.

37. A cell comprising a recombinant nucleic acid of any one of claims 1, 2, 3, 8, 4, 6, 9, 11, 5, 7, 10 or 12.

38. A cell comprising a recombinant nucleic acid of claim 14.

39. A cell comprising a recombinant nucleic acid of claim 15.

40. A cell comprising a recombinant nucleic acid of claim 20.

41. A cell comprising a recombinant nucleic acid of claim 21.

42. A cell comprising a recombinant nucleic acid of claim 23.

43. A cell comprising a recombinant nucleic acid of claim 24.

44. A cell comprising a recombinant nucleic acid of claim 26.

45. A cell comprising a recombinant nucleic acid of claim 27.

* * * * *

SEQUENCE LISTING

<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 1

Asp Phe Asp Leu Asp Met Leu Gly
 1               5

<210> SEQ ID NO 2
<211> LENGTH: 18
<212> TYPE: PRT
<213> ORGANISM: Homo sapiens

<400> SEQUENCE: 2

Asn Phe Leu Gln Leu Pro Gln Gln Thr Gln Gly Ala Leu Leu Thr Ser
 1               5                  10                  15

Gln Pro

<210> SEQ ID NO 3
<211> LENGTH: 6

```
<212> TYPE: PRT
<213> ORGANISM: Homo sapiens

<400> SEQUENCE: 3

Ser Tyr Gly Gln Gln Ser
  1               5

<210> SEQ ID NO 4
<211> LENGTH: 18
<212> TYPE: PRT
<213> ORGANISM: Homo sapiens

<400> SEQUENCE: 4

Asp Phe Ser Ser Ile Ala Asp Met Asp Phe Ser Ala Leu Leu Ser Gln
  1               5                  10                  15

Ile Ser

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 5

Asp Phe Ser Asp Phe Ala Asp Met Asp Phe Asp Ala Asp Leu Ser Gln
  1               5                  10                  15

Ile Ser

<210> SEQ ID NO 6
<211> LENGTH: 11
<212> TYPE: PRT
<213> ORGANISM: Homo sapiens

<400> SEQUENCE: 6

Ala Leu Leu Gln Leu Gln Phe Asp Asp Glu Asp
  1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 7

Ala Leu Leu Asp Leu Asp Phe Asp Asp Glu Asp
  1               5                  10

<210> SEQ ID NO 8
<211> LENGTH: 20
<212> TYPE: PRT
<213> ORGANISM: Homo sapiens

<400> SEQUENCE: 8

Gly Asp Glu Asp Phe Ser Ser Ile Ala Asp Met Asp Phe Ser Ala Leu
  1               5                  10                  15

Leu Ser Gln Ile
              20

<210> SEQ ID NO 9
<211> LENGTH: 20
```

<212> TYPE: PRT
<213> ORGANISM: Artificial Sequence
<220> FEATURE:
<223> OTHER INFORMATION: Description of Artificial Sequence:synthetic
      peptide

<400> SEQUENCE: 9

Gly Asp Glu Asp Ala Ser Ser Ile Ala Asp Met Asp Ala Ser Ala Leu
  1               5                  10                  15

Leu Ser Gln Ile
            20

<210> SEQ ID NO 11
<211> LENGTH: 12
<212> TYPE: PRT
<213> ORGANISM: Homo sapiens

<400> SEQUENCE: 10

Ser Ala Leu Ala Leu Pro Ala Pro Pro Gln Val Leu
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 11

Gly Ala Leu Ala Leu Gly Ala Gly Gly Gln Val Leu
  1               5                  10

<210> SEQ ID NO 12
<211> LENGTH: 11
<212> TYPE: PRT
<213> ORGANISM: Homo sapiens

<400> SEQUENCE: 12

Ser Ala Leu Ala Gln Ala Pro Ala Pro Val Pro
  1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 13

Gly Ala Leu Ala Gln Ala Gly Ala Gly Val Gly
  1               5                  10

<210> SEQ ID NO 14
<211> LENGTH: 13
<212> TYPE: PRT
<213> ORGANISM: Homo sapiens

<400> SEQUENCE: 14

Gly Thr Leu Ser Glu Ala Leu Leu Gln Leu Gln Phe Asp
  1               5                  10

<210> SEQ ID NO 15
<211> LENGTH: 12
<212> TYPE: PRT

```
<213> ORGANISM: Artificial Sequence
<220> FEATURE:
<223> OTHER INFORMATION: Description of Artificial Sequence:synthetic
      peptide

<400> SEQUENCE: 15

Gly Asp Phe Ser Ala Leu Leu Gln Leu Gln Phe Asp
 1               5                  10

<210> SEQ ID NO 16
<211> LENGTH: 9
<212> TYPE: PRT
<213> ORGANISM: Homo sapiens

<400> SEQUENCE: 16

Ser Glu Phe Gln Gln Leu Leu Asn Gln
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 17

Ser Glu Phe Ser Ala Leu Leu Asn Gln
 1               5

<210> SEQ ID NO 18
<211> LENGTH: 9
<212> TYPE: PRT
<213> ORGANISM: Homo sapiens

<400> SEQUENCE: 18

Ser Glu Phe Gln Gln Leu Leu Asn Gln
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 19

Ser Asp Phe Gln Gln Leu Leu Asn Gln
 1               5

<210> SEQ ID NO 20
<211> LENGTH: 13
<212> TYPE: PRT
<213> ORGANISM: Homo sapiens

<400> SEQUENCE: 20

Asp Glu Asp Phe Ser Ser Ile Ala Asp Met Asp Phe Ser
 1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence:synthetic
      peptide
```

```
<400> SEQUENCE: 21

Asp Glu Asp Phe Ser Ser Leu Leu Asp Met Asp Phe Ser
1               5                   10

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5
```